(12) United States Patent
Choo-Smith et al.

(10) Patent No.: US 7,796,243 B2
(45) Date of Patent: Sep. 14, 2010

(54) DETECTION AND MONITORING OF CHANGES IN MINERALIZED TISSUES OR CALCIFIED DEPOSITS BY OPTICAL COHERENCE TOMOGRAPHY AND RAMAN SPECTROSCOPY

(75) Inventors: Lin-P'ing Choo-Smith, Winnipeg (CA); Alex C. T. Ko, Winnipeg (CA); Mark Hewko, Winnipeg (CA); Lorenzo Leonardi, Winnipeg (CA); Blaine Cleghorn, Bedford (CA); Cecilia Dong, Winnipeg (CA)

(73) Assignees: National Research Council of Canada, Ottawa, Ontario (CA); Dalhousie University, Halifax, Nova Scotia (CA); University of Manitoba, Winnipeg, Manitoba (CA)

( * ) Notice: Subject to any disclaimer, the term of this patent is extended or adjusted under 35 U.S.C. 154(b) by 484 days.

(21) Appl. No.: 11/148,422

(22) Filed: Jun. 9, 2005

(65) Prior Publication Data
US 2005/0283058 A1 Dec. 22, 2005

Related U.S. Application Data

(60) Provisional application No. 60/578,070, filed on Jun. 9, 2004.

(51) Int. Cl.
*G01N 21/00* (2006.01)
(52) U.S. Cl. ...................................................... 356/72
(58) Field of Classification Search ......... 356/301–334, 356/402–425; 600/310, 407, 479, 315, 476, 600/473, 478
See application file for complete search history.

(56) References Cited

U.S. PATENT DOCUMENTS

| | | | | |
|---|---|---|---|---|
| 6,002,480 A * | 12/1999 | Izatt et al. | ...................... | 356/479 |
| 6,507,747 B1 * | 1/2003 | Gowda et al. | ................ | 600/407 |
| 6,593,101 B2 * | 7/2003 | Richards-Kortum et al. | .. | 435/29 |
| 6,618,152 B2 * | 9/2003 | Toida | .......................... | 356/479 |
| 2002/0016533 A1 * | 2/2002 | Marchitto et al. | ........... | 600/310 |
| 2004/0260183 A1 * | 12/2004 | Lambert et al. | .............. | 600/476 |

* cited by examiner

*Primary Examiner*—Tarifur R. Chowdhury
*Assistant Examiner*—Isiaka O Akanbi
(74) *Attorney, Agent, or Firm*—Adrian D. Battison; Ade & Company Inc.

(57) ABSTRACT

Early dental caries detection is carried out by a method that combines optical coherence tomography (OCT) and Raman spectroscopy to provide morphological information and biochemical specificity for detecting and characterizing incipient carious lesions found in extracted human teeth. OCT imaging of tooth samples demonstrated increased light backscattering intensity at sites of carious lesions as compared to the sound enamel. Raman microspectroscopy and fibre-optic based Raman spectroscopy are used to characterize the caries further by detecting demineralization-induced alterations of enamel crystallite morphology and/or orientation. OCT imaging is useful for screening carious sites and determining lesion depth, with Raman spectroscopy providing biochemical confirmation of caries. The combination is incorporated into a common probe operable without movement to scan the tooth surface and to provide an output for the dentist.

40 Claims, 24 Drawing Sheets

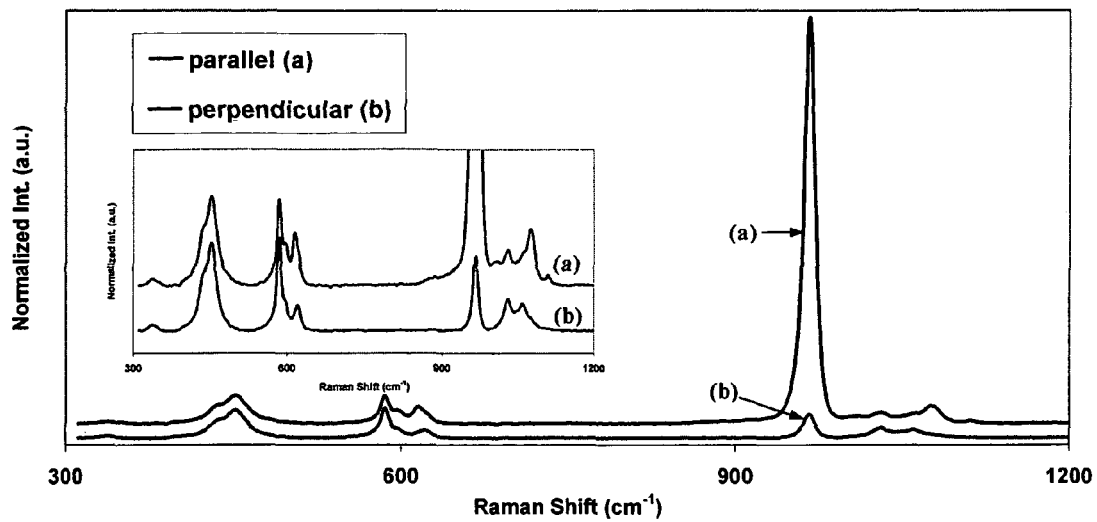
Figure 13. Polarized Raman spectra of sound enamel using (a) parallel and (b) perpendicular polarization
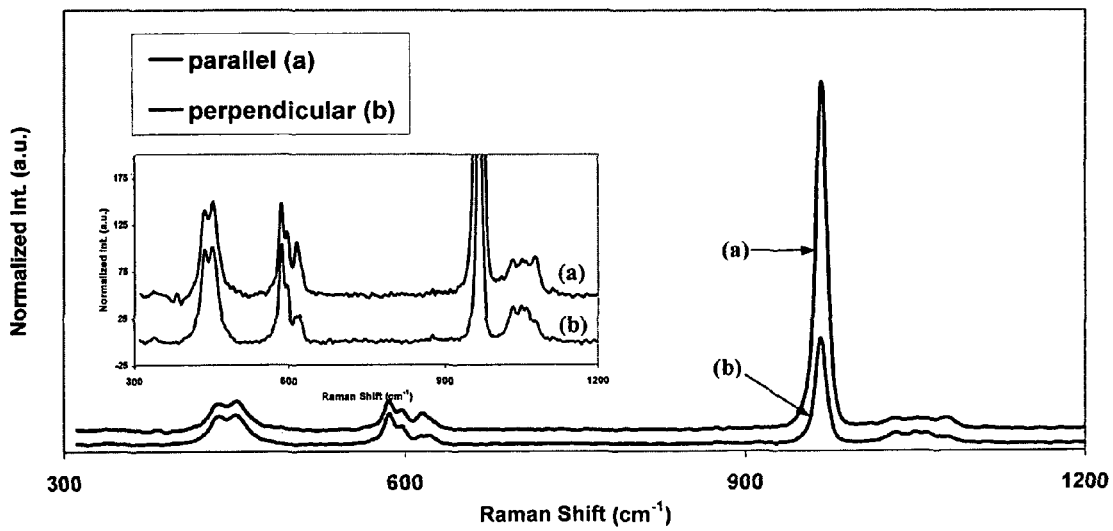
Figure 14. Polarized Raman spectra of carious enamel using (a) parallel and (b) perpendicular polarizations

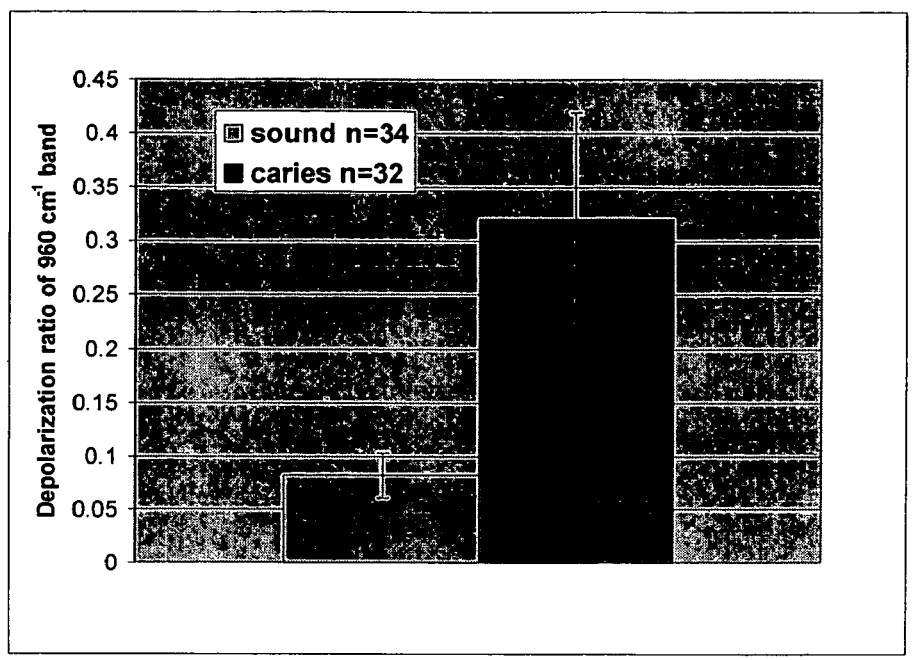

Figure 15. Bar graphs demonstrating the depolarization ratio (ρ) of the 960 cm$^{-1}$ band from spectra obtained from sound vs. carious enamel. Mean +/- standard deviation values are shown; P<0.01, student t-test.

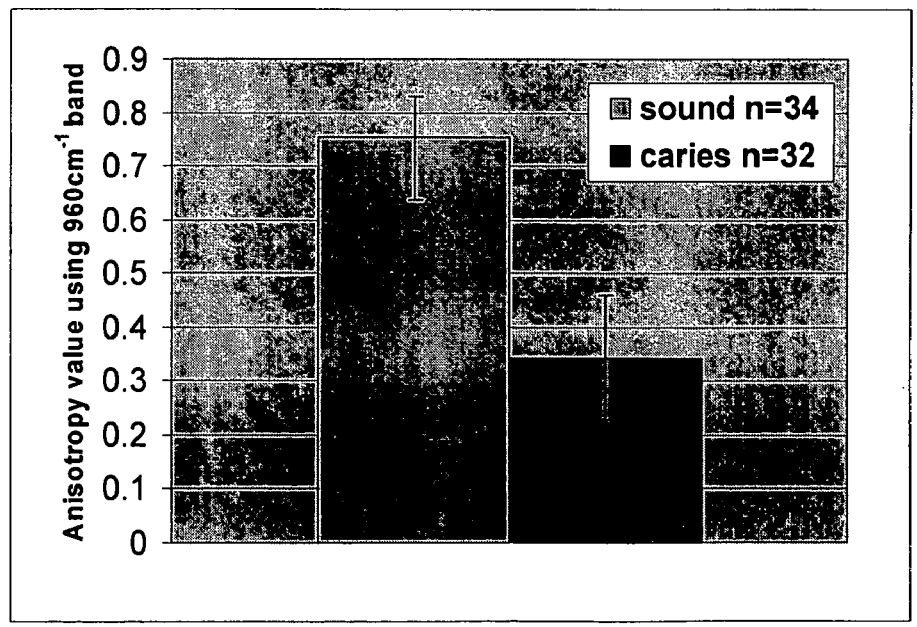

Figure 16. Bar graphs demonstrating the index of orientation (A) of the 960 cm$^{-1}$ band from spectra obtained from sound vs. carious enamel. Mean +/- standard deviation values are shown; P<0.01, student t-test.

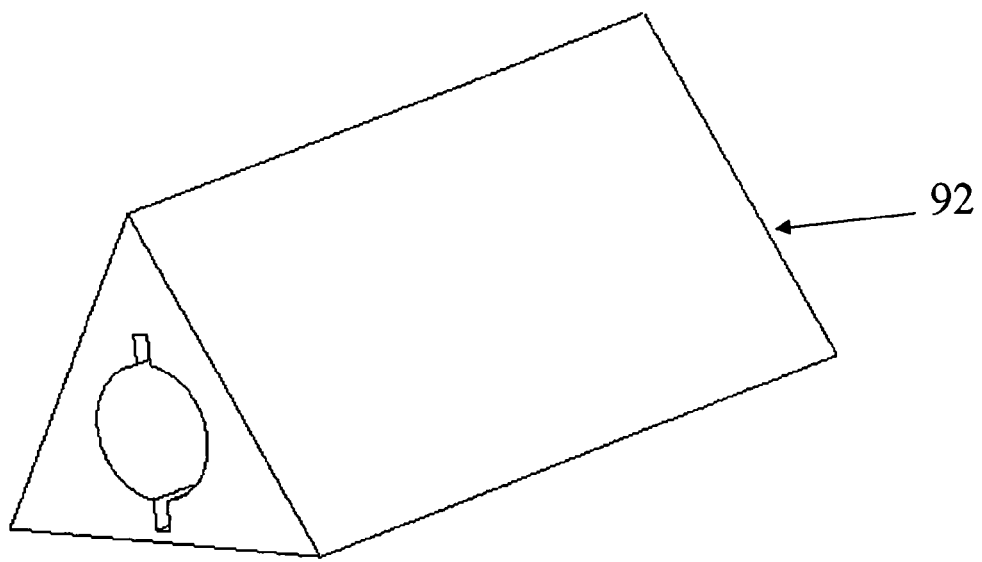
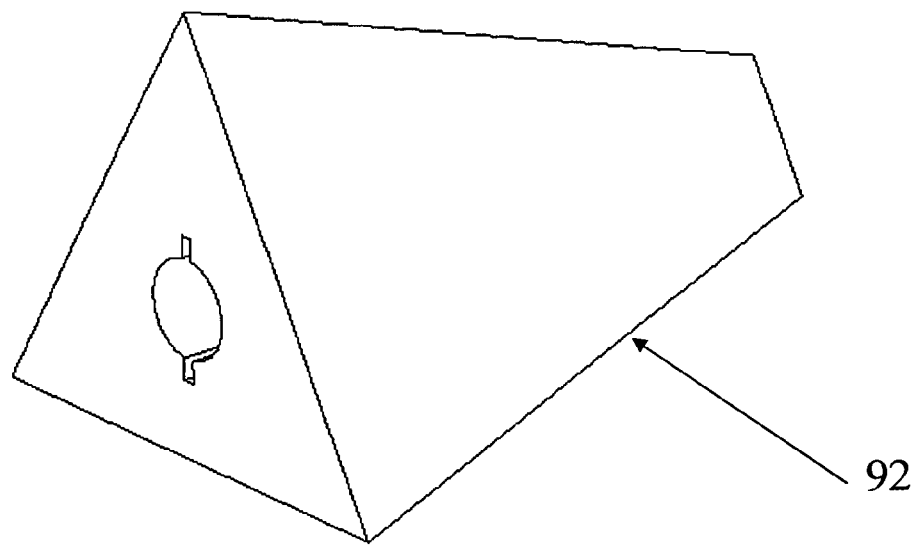
Figure. 25

Table 1.

| | OHAp[a] | OHAp[b] | OHAp[c] | Enamel[a] | Enamel[d] | Enamel[b] | Enamel[c] | Enamel[e] |
|---|---|---|---|---|---|---|---|---|
| $v_2\ PO_4^{3-}$ | 430 | 432 | 433 | 431 | 431 | 430 | 433 | 430 |
| | 447 | 449 | 448 | 446 | 446 | 446 | 450 | 448 |
| $v_4\ PO_4^{3-}$ | 581 | 581 | 580 | 579 | 582 | 577 | 579 | 581 |
| | 591 | 593 | 591 | 590 | 589 | 590 | 588 | 590 |
| | 608 | 609 | 607 | 608 | 608 | 606 | 608 | 609 |
| | | 617 | 614 | 614 | | 615 | | |
| $v_1\ PO_4^3$ | 962 | 962 | 964 | 959 | 961 | 959 | 959 | 960 |
| $v_3\ PO_4^{3-}$ | 1029 | 1028 | 1029 | 1023 | 1023 | 1024 | 1026 | 1032 |
| | | 1043 | 1041 | | | | | 1041 |
| | 1046 | 1048 | 1048 | 1043 | 1042 | 1043 | 1043 | 1045 |
| | | 1055 | 1057 | 1052 | | 1050 | | |
| | | | 1064 | | | | | |
| | 1076 | 1077 | 1077 | 1069 | 1070 | 1070 | 1071 | 1071 |
| type-A $v_1 CO_3^{2-}$ | | | | 1104 | 1104 | | 1103 | |
| type-B $v_1 CO_3^{2-}$ | | | | 1069 | 1070 | 1071 | 1071 | |

[a] Raman microspectroscopy, current study
[b] ref. 36
[c] ref. 44
[d] fibre-optic Raman spectroscopy, current study
[e] ref. 22

DETECTION AND MONITORING OF CHANGES IN MINERALIZED TISSUES OR CALCIFIED DEPOSITS BY OPTICAL COHERENCE TOMOGRAPHY AND RAMAN SPECTROSCOPY

This application claims priority under 35 U.S.C. 119 from U.S. Provisional Application Ser. No. 60/578,070 filed Jun. 9, 2004.

This invention relates to a method for detecting, monitoring and assessing changes in mineralized tissues or calcified deposits by optical coherence tomography and Raman spectroscopy. The invention is primarily but not exclusively designed for use in detecting early caries in tooth structures.

BACKGROUND OF THE INVENTION

Calcification is the process whereby the mineral calcium builds up in tissue, causing it to harden. Calcium that enters the body is normally deposited in bones and teeth (i.e. mineralized tissues). Ossified (hardened) tissues such as bone and teeth are composed of calcium phosphate and calcium carbonate deposits. In particular, the bulk of the mineral phase of bones and teeth is a poorly crystalline carbonate-rich analogue of the naturally occurring mineral hydroxyapaptite. When there is an imbalance in the body, calcium and other minerals can be deposited in other parts of the body such as arteries, aortic valves, kidneys, lungs, breast, brain, cartilage and tendons. Such deposits can disrupt the normal function of these tissues.

The calcification of healthy mineralized tissues results in ordered structures such as the hydroxyapatite rods found within dental enamel and dentin. However, in diseased states such as upon the attack of acid by acid-forming bacteria, the ordered structure is disturbed creating porous regions and amorphous areas.

Dental caries (i.e. dental cavities or dental decay) is a common oral disease that many people have experienced at some point in their life. With the introduction of fluoride in drinking water and toothpastes, there has been a decline in the prevalence of dental caries in Western countries.[1] However, a recent report states that caries still remains a large problem in specific population groups (e.g. minority children, the economically underprivileged, older people, the chronically ill and institutionalized persons).[2] Furthermore, the patterns of caries development are changing, to those with smaller lesion sizes and slower progression rates, making caries more difficult to detect with existing conventional techniques.[1] This is further complicated when caries develop at locations which are not clinically visible (e.g. between adjacent teeth). Current diagnostic methods involve subjective clinical criteria (colour, "softness", resistance to removal) and the use of tools such as the dental explorer and dental radiographs. Such methods may not be reliable for detecting interproximal lesions (those between adjacent teeth) because these carious lesions are not clinically visible. In addition, these clinical methods do not adequately detect changes in caries development and do not possess the sensitivity, specificity nor ability to account for the dynamic process of demineralization-remineralization.[1,2] Therefore, more refined diagnostic tools are required to identify early non-cavitated carious lesions and to monitor their activity as well as severity. Early caries detection can potentially increase the implementation of conservative treatment methods centred on tooth preservation rather than restoration. Conservative methods include non-surgical interventions such as fluoride to promote remineralization, antimicrobials to arrest caries activity and sealants to prevent dental caries. New diagnostic techniques will enable the clinician to monitor patients for further lesion demineralization or remineralization, to evaluate the effectiveness of treatment strategies, as well as to encourage patient compliance in following suggested preventive measures. Several methods addressing the need for better early dental caries diagnostic tools with improved sensitivity and specificity have been investigated and recently reviewed.[3-6] Among the methods are direct digital radiography (DDR), digital imaging fibre-optic trans-illumination (DIFOTI), electroconductivity measurements (ECM), quantitative light-induced fluorescence (QLF) and laser fluorescence.[3] DDR has the capability to optimize diagnostic imaging operation by eliminating the need for film processing as well as to reduce the potential patient radiation dose. Although the technique uses a lower radiation dose, the application of the method is still limited by the ionizing radiation required to obtain an image. Like conventional radiographs, the technique provides little value in the detection of initial enamel lesions.[3] DIFOTI, marketed by Electro-Optical Sciences, involves a trans-illumination technique through the use of a fibre-optic device to shine light on the tooth. The image captured represents the scattered and absorbed light as it traversed the tooth. Although the technique can detect incipient caries, the method is subjective, relying on the expertise of the examiner with a high level of intra- and inter-examiner variability.[3,7]

Another technique, ECM is based upon the observation that sound surfaces have limited or no conductivity whereas surfaces with caries will have measurable conductivity that will increase with increasing demineralization. The drawback of the technique is its lack of specificity, which limits its usefulness in deciding whether or not to treat a lesion operatively. The low specificity increases the chance of false-positive results which translate into possibly unnecessary invasive treatment.[5] Perhaps the most advanced of the technologies available is that based on fluorescence spectroscopy. With quantitative light-induced fluorescence, light at 488 nm is shone on a tooth and induces a natural fluorescence. Areas of demineralization appear as dark spots with mineral loss correlating with a relative loss of fluorescence radiance. With this method, the presence of bacterial plaque or saliva interferes with the usefulness of the technique.[8] A related approach, laser fluorescence, uses light at 633 nm and the reflected fluorescence is measured. The light interacts with the bacterially produced porphyrins that leach into the decayed regions. Therefore fluorescence is suggestive of decay present. This is the basis for the commercially available DIAGNOdent device by KaVo. Recent clinical studies indicate that this latter technique can lead to false-positive results due to the presence of stains, deposits, calculus and organic material in the region of interest[9] and is not suitable for detecting initial carious changes in enamel.[10] Therefore, despite the potential of these various technologies, the methods are prone to subjectivity issues with high intra- and inter-examiner variability, false-positive results due to stains or organic deposits and the unsuitability for detecting initial enamel caries at interproximal sites. As a result of these shortcomings, more refined tools with improved sensitivity and specificity are needed for early detection of interproximal dental caries.

SUMMARY OF THE INVENTION

It is one object of the invention to provide a method for the detection and monitoring of changes in mineralized tissues or calcified deposits.

According to one aspect of the invention there is provided a method for detecting and monitoring changes in mineralized tissues or calcified deposits comprising:

scanning an area of tissue using optical coherence tomography (OCT) to generate OCT data used for detection and assessment;

and using Raman spectroscopy over at least part of the area to generate Raman data used to detect, confirm or monitor the change therein.

Preferably the OCT is used to scan a whole area for areas of interest and the Raman spectroscopy is used only in the areas of interest identified by the optical coherence tomography.

Preferably the OCT and the Raman spectroscopy are carried out using a common probe.

Preferably the OCT and the Raman spectroscopy are carried out without moving the probe between measurements.

Preferably the OCT and the Raman spectroscopy are carried out sequentially.

Preferably the OCT uses non-polarized or polarized (PS-OCT) light.

Preferably the OCT data is used to provide morphological details comprising:
Size
Depth within tissue
Shape
Border delineating area of interest from surrounding material
Indication of heterogeneity of sample
Presence of cracks or defects
Boundary between different tissue layers or tissue types Preferably Raman spectroscopy data is used to provide biochemical information for confirming that regions arising from genetic or developmental malformations detected by the optical coherence tomography as areas of interest are false-positive results of early diseased states.

Preferably the Raman spectroscopy is carried out at a wavelength in the near-infrared range (e.g. 830 nm within 750 nm-2500 nm range) as the background biological fluorescence is lower in this range.

Preferably the wavelength of 750 nm-1000 nm allows for Raman signal detection by silicon-based detectors (CCD).

Preferably the detection and monitoring in the Raman spectroscopy is carried out using biochemical information derived from the ratio of various selected Raman peaks to the P-O symmetric stretching vibration (nu1 peak) of hydroxyapatite (e.g. ~930 $|cm^{-1}|$-1000 $cm^{-1}$) peak.

Preferably the Raman spectroscopy uses selected peaks specific to Raman bands arising from hydroxyapatite found within mineralized tissues and calcified deposits, comprising Raman shift in the spectral regions between 200-1200 $cm^{-1}$ (examples include, but not limited to, the regions of 200-400 $cm^{-1}$, 400-500 $cm^{-1}$, 500-600 $cm^{-1}$, 930-1000 $cm^{-1}$, and 1000-1100 $cm^{-1}$)

Preferably the Raman spectroscopy uses non-polarized or polarized light.

Preferably polarization-coupled techniques are used to quantitate the change in demineralization and remineralization which alter the birefringent properties of the sample.

Preferably the Raman spectroscopy uses polarized light and compares signals with parallel polarized and perpendicular polarized light comprising:
determining the depolarization ratio, $\rho$ $$\rho = I_{(\perp)}/I_{(\parallel)}$$

where $I_{(\perp)}$ and $I_{(\parallel)}$ are the integrated peak intensities of the P-O symmetric stretching vibration (nu1 peak) of hydroxyapatite (e.g. ~930 $|cm^{-1}|$-1000 $cm^{-1}$) in orthogonally polarized Raman spectra.

Preferably the Raman spectroscopy uses polarized light and compares signals with parallel polarized and perpendicular polarized light and quantification of the anisotropic difference is achieved by using the following equation:

$$A = (1-\rho)/(1+2\rho) \text{ with } \rho = I_{(\perp)}/I_{(\parallel)}$$

or $$A = (I_{(\parallel)} - I_{(\perp)})/(I_{(\parallel)} + 2I_{(\perp)})$$

Where A is anisotropy or sometimes called the conventional index of orientation.

Preferably the Raman spectroscopy is used to detect changes in structure, orientation and/or chemistry of the hydroxyapatite crystals and/or rods in the sample.

Preferably the Raman spectroscopy data is used to provide information of the mineralization state:
Active or arrested dental caries
Degree of demineralization
Degree of remineralization
Degree of hypermineralization Preferably the method is used for detecting and monitoring changes in tooth enamel or dentin for the detection of dental caries.

Preferably the OCT and Raman spectroscopy data are used in analysis of dental caries to provide quantitative information about the dental caries comprising:
Estimate of the lesion depth
degree of demineralization based on the depolarization ratio or anisotropy or conventional index of orientation
degree of remineralization and hypermineralization based upon the intensity of the $CaF_2$ peak around 300-350 $cm^{-1}$ in the Raman spectrum arising from calcium fluoroapatite upon remineralization Preferably there is provided a high coherent light source for the Raman measurements which is also capable of wavelength sweeping to provide broadband light energy for the OCT measurements.

Preferably the light energy is delivered to the sample and signal collected from the sample via at least one fibre optic cables interfaced with an ergonomically-shaped dental handpiece probe with an intra-oral portion and wherein a probe shaft is wrapped in disposable sterile sheath.

Preferably the light energy is delivered to the sample and signal collected from the sample via at least one fibre optic cables interfaced with an ergonomically-shaped dental handpiece probe with an intra-oral portion and wherein the same fibre optic is used for delivery and collecting the light to and from the sample through the use of fibre optic combiners and/or circulators.

Preferably the light energy is delivered to the sample and signal collected from the sample via at least one fibre optic cables interfaced with an ergonomically-shaped dental handpiece probe with an intra-oral portion and wherein the probe contains optical components enabling controlling the transmission and reception of light energy so that the area of interest is scanned.

Preferably the probe optical components consists of micromirrors such as micro-electronic mirrors (MEMS) or micro-optoelectrical mirrors (MOEMS) or galvanometer devices to allow steering of the light beam in a 2-dimensional (e.g. X-Y) pattern on the area of interest and a micro-mirror switcher to toggle between OCT and Raman measurements.

Preferably the light energy is delivered to the sample and signal collected from the sample via at least one fibre optic cables interfaced with an ergonomically-shaped dental handpiece probe with an intra-oral portion and the probe contains a micro-mirror motor or switcher allowing rotation of the mirror sets to enable sequential measurements from two adjacent surfaces of the distal and mesial surfaces of a tooth.

Preferably the probe contains an indicator of which surface is currently under investigation.

Preferably the light energy is delivered to the sample and signal collected from the sample via at least one fibre optic cables interfaced with a dental handpiece probe with an intra-oral portion and wherein the probe contains optical filters such as bandpass filters for selecting the wavelengths of interest for Raman measurements or optical filters such as longpass filter, edge filter or notch filters or fibre Bragg gratings for blocking/suppressing the Rayleigh scatter and transmitting the Raman scattered signal.

Preferably the light energy is delivered to the sample and signal collected from the sample via at least one fibre optic cables interfaced with an ergonomically-shaped dental handpiece probe with an intra-oral portion and wherein the probe contains optical components to allow optional polarization studies such as linear polarizers, analyzers, waveplates and birefringent optics.

Preferably the light energy is delivered to the sample and signal collected from the sample via at least one fibre optic cables interfaced with an ergonomically-shaped dental handpiece probe with an intra-oral portion and wherein the probe contains a probe head and tip arranged to enable imaging/measurements in the gingival embrasure of the interproximal spaces between adjacent teeth, the tip having a triangular shaped tip with a triangular cross-section to allow the tip to be wedged into tight spaces such as the gingival embrasures between teeth, the tip being formed of a material that allows transmission and collection of light energy with minimal disruption.

Preferably the probe tip is capable of rotating 180 degrees for functioning such as in all four quadrants of a mouth.

Preferably there is provided a portable LCD control box which can provide data analysis to overlay data and produce user-friendly data for clinicians/operators (e.g. 3 colour indicator, severity indicator, etc.)

Preferably the OCT detection is used to generate images which are processed allowing automatic determination of the sample surface, determination of the DEJ, determination of the scattering intensity in order to arrive at a quantitative value regarding:

Presence of an intact surface
Lesion depth
Thickness of the surface layer.

Preferably the OCT detection is arranged such that there are image registration markers enabling the use of time series of OCT images to allow spatial registration of data collected for monitoring and comparison purposes where such information relays information of lesion progression, arrest, reduction, demineralization and remineralization.

Preferably the Raman data is processed to obtain depolarization ratio values and/or anisotropy index of orientation values useful for
Indicating the presence of sound enamel
Indicating the presence of early dental caries
Indicating the severity of the dental caries Preferably the Raman data is processed to obtain the level of remineralization from the intensity of the CaF2 fluoroapatite peak at ~321 $cm^{-1}$.

Preferably there is provided a user interface in the form of an LDC control box for data acquisition which includes an LCD screen display for displaying which surface of a tooth is under test and which quadrant/tooth number.

Preferably there is provided a user interface in the form of an LDC control box for data acquisition which includes separate indicators indicative of no decalcification, decalcification and intact surface and cavitation together with a numerical scale to indicate depth or severity of demineralization.

Preferably there is provided a handpiece which contains separate indicators indicative of no decalcification, decalcification and intact surface and cavitation.

Preferably the Raman detection is carried out using a sweeping of the source wavelength which is used by the Raman system to collect data from multiple excitation wavelengths (e.g. differing by 1 nm) in order to mathematically remove the background fluorescence signals by taking a difference of the data acquired at each wavelength and integrating the resulting difference to produce Raman data free of the background fluorescence.

The invention thus provides a method involving optical coherence tomography (OCT) and Raman spectroscopy to provide morphological information and biochemical specificity important for detection and monitoring of changes which are associated with diseased states of mineralized tissues and calcified deposits.

The synergy is important to the operation of the two techniques in that, more than merely adding two techniques but really one feeding off the other, i.e. Raman requires initial detection of location with OCT, OCT requires Raman confirmation to reduce possibilities of false-positive results (e.g. hypocalcified regions on OCT image resemble early caries, but is really a genetic malformation).

The device described herein is useful for detection/monitoring/diagnosis of mineralized tissues or calcified deposits via use of a fibre optic based probe including a specialized probe tip (e.g. probe configuration, detail for imaging two proximal surfaces, LCD display unit, toggle switches, illumination on probe handle). The method and device will be described in detail for an application within dentistry, namely dental caries detection and monitoring. However, due to the similar nature of the composition and structure of mineralized tissues and calcified deposits, the overall method and probe described herein can be applied to any mineralized tissue or calcified deposit for detecting the presence of the deposit and for detecting and monitoring changes within the deposits or mineralized tissues.

The method and device as described herein can in most cases do all of the following:

detect early interproximal caries (via probe device with OCT or PS-OCT);

assess lesion depth (via OCT or PS-OCT);

provide indication of intact surface or cavitated lesion (via OCT or PS-OCT);

provide biochemical specificity due to mineral component itself irrespective of staining, saliva, organic components (via RS or P-RS);

reveal degree of demineralization (via RS or P-RS) reveal degree of hypermineralization or remineralization (via RS or P-RS);

provide knowledge of the dynamic demineralization-remineralization process;

be used for monitoring treatment measures (in re-mineralization) and patient compliance (whole device).

A dental device using the methods described herein can be used:

in all dental offices as part of routine check-ups;

as a fibre optic-based dental probe/method to obtain clinically useful information from early incipient caries at interproximal sites not clinically visible;

as a device for quantitating the de-/re-mineralization of caries to allow patient monitoring;

to provide non-ionizing radiation which allows more frequent checks on the caries;

to encourage patient compliance to follow suggested hygiene measures;

in dental teaching universities to encourage the new focus of preventative dentistry rather than traditional restorative (drill & fill) approach. Many early caries are being unnecessarily restored since it is uncertain if the lesion has cavitated and mostly these non-cavitated ones can be saved by first re-mineralization.

The advantages of detecting early caries non-subjectively with this device are:

aid in diagnosis/clinical decision making i.e. determine if the caries has cavitated or not assist in decision to restore or not (choice for re-mineralization options)

if cavitated, surgical procedures can be implemented early before it gets any further resulting in pain, suffering, more costly procedures that undermine tooth structure.

if non-cavitated, clinical decisions with respect to treatment strategies can be made, e.g. employing non-surgical methods such as fluoride to promote re-mineralization, anti-microbials, sealants; such approaches represent a new focus in dental care on tooth preservation rather than restoration if non-surgical methods are employed, technology can be used to monitor efficacy of treatment strategies The method thus initially proposes that the combination of an optical and a spectroscopic technique, namely, optical coherence tomography and Raman spectroscopy, has the potential to be developed as a fibre-optic tool for early detection of dental caries. Optical coherence tomography (OCT) can provide morphological information for dental caries detection similar to the conventional images with which dental clinicians are familiar. Raman spectroscopy furnishes biochemical specificity because it is based on spectral peaks specific to the (bio)chemical and structural properties of tooth mineralization and not to staining or organic matter. Combining the two technologies takes advantage of their synergies for detecting lesions and for providing objective biochemical information. In so doing, the limitations of using a single method alone can be minimized and potentially overcome, thereby yielding an approach with greater sensitivity for early dental caries detection.

To better understand how OCT and Raman spectroscopy are well suited for caries detection, it is useful to examine the nature of dental caries development. In particular, the focus will be on dental caries of the enamel which is the highly mineralized tissue covering the tooth crown. Dental caries arises from the destruction of tooth structure by acid-forming bacteria found in dental plaque. The early dental carious lesion (incipient caries) is non-cavitated and limited to the outer enamel surface. This caries type presents as a visible "white spot" when the tooth is air-dried. Histological studies have shown that white-spot lesions consist of 4 regions or layers.[11,12] The first region (the enamel surface of the incipient lesion) is intact and well mineralized. The second region which lies immediately beneath the highly mineralized surface layer is very porous (25-50% porosity by volume) and is the largest of the 4 regions. The third region (the dark zone) does not transmit polarized light (also known as positive birefringent) because it consists of many tiny pores as well as inter-prismatic areas and cross-striations. The fourth or deepest region is the translucent zone. It is the advancing front of the enamel lesion and appears structure-less when examined with polarized light. Compared with the subsurface, the surface zone (~30 μm thick) contains more fluoride, less water, less carbonate, is more highly mineralized and the enamel crystals are often larger and oriented differently from those below.[11] Such properties render the enamel surface more resistant to acid attack. This surface layer is also partly formed by re-mineralization in which dissolved ions (calcium and phosphate) originating from the subsurface region and saliva are deposited into the surface layer. The original crystalline framework of the enamel rods serves as a nucleating agent for re-mineralization. Depending on the extent of demineralization, enamel caries can extend from a depth of ~100-250 μm (for incipient caries) to entirely through the enamel at which point the cavitated lesion (~1.5 mm deep) has just extended into the underlying dentin.[13] The enamel itself is an acellular tissue composed of 80-90% by volume of crystals of carbonated calcium hydroxyapatite [$Ca_{10}(PO_4)_6(OH)_2$ where $PO_4^{3-}$ or $OH^-$ can be substituted by $CO_3^{2-}$], with the remaining 10-20% being fluid and organic (mainly proteinaceous) material.[11] The carbonated apatite crystals are arranged into bundles to form rods or prisms with inter-crystalline spaces between rods that allow diffusion of ions during the caries process. The structural and biochemical changes associated with enamel caries development suggest that OCT imaging and Raman spectroscopic techniques offer potential for differentiating between sound (i.e. healthy) and carious enamel.

OCT is a non-invasive technique that provides high-resolution depth imaging of near surface tissue structures. Similar to ultrasound in operation but offering an order of magnitude of greater spatial resolution, OCT provides morphological images with 20 μm resolution to depths of ~2 mm.[14] Current dental x-rays have a resolution of 50 μm and superimpose the entire three-dimensional tooth structure onto a two-dimensional film. Dental applications of OCT have demonstrated its potential for in vivo imaging of intra-oral tissue such as delineating structural components of gingival tissue (e.g. sulcus, epithelium, connective tissue layer) as well as hard tissue structures (e.g. enamel, dentin and the dentin-enamel junction).[14-17] More recently, polarization sensitive OCT (PS-OCT) with near-infrared excitation has been used to image dental tissue carious lesions and has demonstrated the potential of the technique for monitoring the progression of lesions over time.[15,17-19] OCT is therefore well suited for detecting morphological changes in teeth arising from caries formation. Our approach of combining Raman spectroscopy with OCT will add biochemical specificity providing important information for resolving the structural features observed with OCT imaging thereby reducing false-positive observations.

Raman spectroscopy is a vibrational spectroscopic technique that provides details on the biochemical composition, molecular structure and molecular interaction in cells and tissues.[20] Highly specific biochemical information about proteins, lipids, carbohydrates, nucleic acids and in this case, mineral orientation and composition (e.g. $PO_4^{3-}$, $CO_3^{2-}$), can be obtained.[21,22] Raman is well suited to examine mineralized tissues and has been used previously by various research groups to study bone and teeth; for example to understand the mechanical properties of bone, mineralization of hydroxyapatite and the effects of post-extraction treatment of teeth.[21-28] Earlier studies characterizing dentin and enamel structures and their interfaces with resin and bonding agents, have shown that Raman spectra of tooth enamel and dentin exhibit peaks characteristic of the inorganic (i.e. hydroxyapatite) and organic (e.g. collagen in dentin) components of teeth as well as quantitative chemical information of the adhesive interface. [29,35] Polarized Raman spectroscopy used to study the fundamental structural characteristics of tooth enamel crystallites have observed differences due to crystal orientation.[36,37] The application of near-infrared (785 nm) fibre-optic Raman spectroscopy to characterize advanced dental caries has shown spectral differences between sound and carious regions of teeth based upon Raman peaks superimposed on a broad luminescence background of unknown origin.[38,39] The background fluorescence is problematic for Raman spectroscopy, often masking peaks of interest and is not a solid basis for differentiating healthy from carious teeth. Fluorescence changes might arise from stains and food particles trapped within the carious regions. In our studies, the strengths of the biochemical specificity of Raman spectroscopy will be used by examining spectral peaks characteristic of hydroxyapatite within mineralized dental tissue.

Various studies using OCT and Raman spectroscopy are provided to detect and characterize early enamel carious lesions in extracted human teeth. Comparisons will be made with results obtained from sound tooth enamel. The Raman studies are conducted with microspectroscopy, polarized Raman spectroscopy and fibre-optic sampling to illustrate the similarity of the information obtained with both (microscopy and fibre-optic) measurement modes and the potential of developing the Raman technique combined with OCT, into a fibre based tool for clinical applications with improved sensitivity and specificity.

According to a further aspect of the invention which may be pursued in a separate application to be filed as a continuation application there is provided a method for detecting and monitoring changes in mineralized tissues or calcified deposits comprising using Raman spectroscopy (non-polarized or polarized) over at least part of the area to detect changes in structure, orientation and/or chemistry of hydroxyapatite crystals and/or rods in the tooth. Yet further preferred but important features of this aspect of the invention are defined above in relation to the Raman detection and the analysis and use of the data obtained thereby and the probe by which the testing is made.

According to a further aspect of the invention which may be pursued in a separate application to be filed as a continuation application there is provided a method for detecting and monitoring changes in mineralized tissues or calcified deposits comprising using OCT (non-polarized or polarized). Preferred but important features of this aspect of the invention are defined above in relation to the OCT detection and the analysis and use of the data obtained thereby and the probe by which the testing is made.

According to a further aspect of the invention which may be pursued in a separate application to be filed as a continuation application there is provided an apparatus for detecting and monitoring changes in mineralized tissues or calcified deposits comprising using a probe and display system, important features of which aspect of the invention are defined above.

The above separate aspects do not rely or may not rely on the combination of the OCT and Raman Spectroscopy and thus may be independent of that feature.

BRIEF DESCRIPTION OF THE DRAWINGS

Embodiments of the invention will now be described in conjunction with the accompanying drawings in which:

FIG. 13 is a polarized Raman spectra of sound enamel using (a) parallel and (b) perpendicular polarization FIG. 14 is a polarized Raman spectra of carious enamel using (a) parallel and (b) perpendicular polarizations FIG. 15 is a bar graph demonstrating the depolarization ratio (p) of the 960 $cm^{-1}$ band from spectra obtained from sound vs. carious enamel. Mean +/−standard deviation values are shown; P<0.01, student t-test.

FIG. 16 is a bar graph demonstrating the index of orientation (A) of the 960 $cm^{-1}$ band from spectra obtained from sound vs. carious enamel. Mean +/−standard deviation values are shown; P<0.01, student t-test.

FIG. 25 shows isometric views of the alternative cross-sectional shape of the tip of the probe of FIG. 24.

Figure 1:
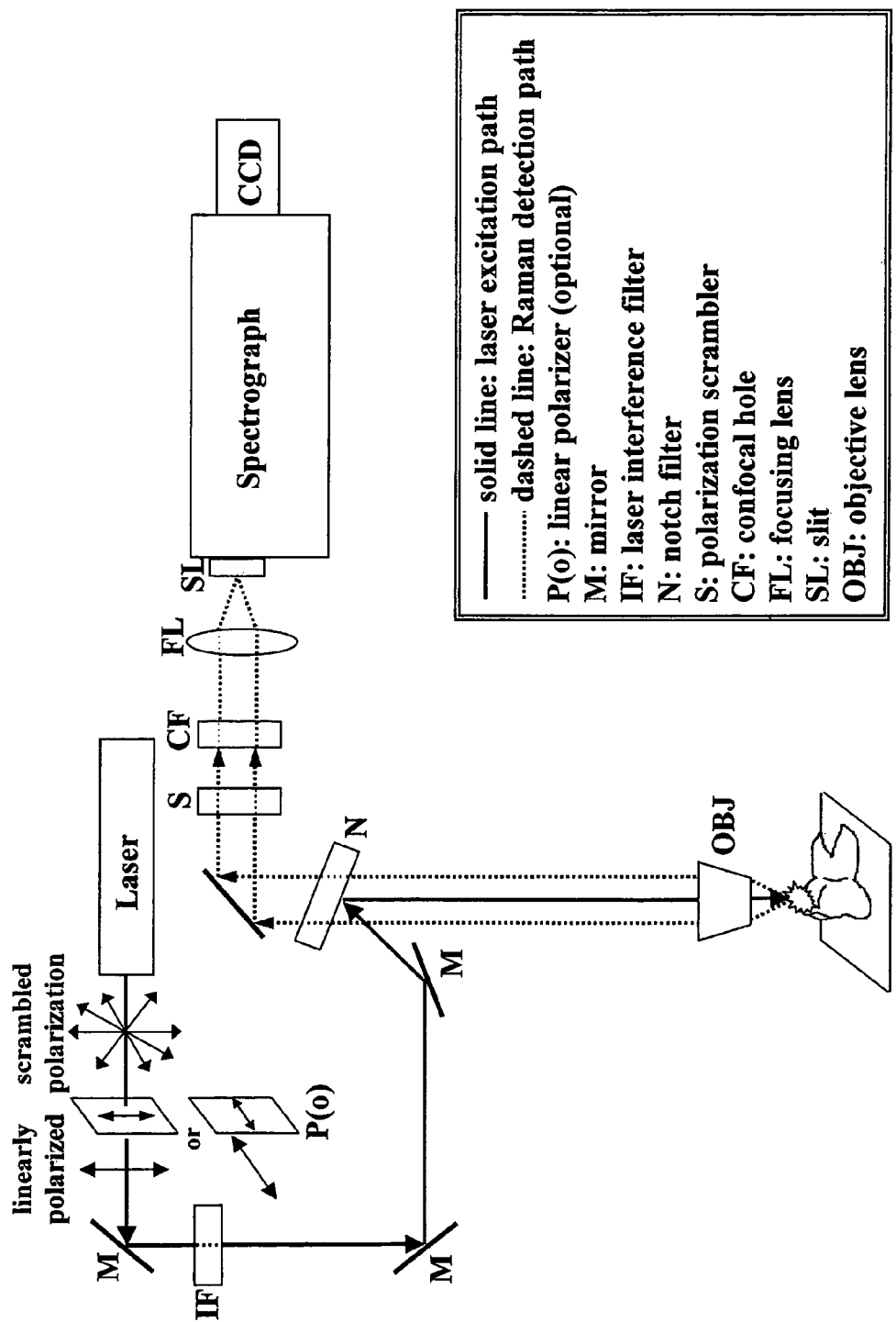
FIG. 1 is a schematic diagram of the Raman microspectroscopic system illustrating the laser excitation (solid line) and Raman signal detection (dashed line) paths for acquiring tooth spectra in an 180° geometry. Abbreviations are provided in the insert for each optical element. The linear polarizer (P) is only used when performing polarized Raman experiments.

Table 1 is Raman peak positions and tentative band assignments of human tooth enamel and synthetic hydroxyapatite (OHAp) compared with previous studies in the literature.

DETAILED DESCRIPTION

Human molars and premolars (n=15) were collected from orthodontic patients at the Dental Clinic of the Faculty of Dentistry, University of Manitoba. Approvals from the human ethics committees of the Institute for Biodiagnostics (National Research Council Canada), University of Manitoba and Dalhousie University were obtained prior to sample collection. All teeth were examined in patients before extraction and no discoloration of the marginal ridge was observed. Remaining soft tissue on extracted teeth was removed by scaling and the samples were thoroughly rinsed with water. Teeth were preserved in sterile filtered de-ionized water until measurement. Each tooth sample was radiographed and independently re-assessed ex vivo by two clinical investigators at the University of Manitoba and Dalhousie University, respectively. Control caries-free teeth had no visible decalcification or demineralization. Incipient carious teeth included regions of decalcification with intact surfaces and opacity of enamel. Among the 15 extracted teeth, 10 were identified to be carious teeth with at least 15 caries sites in total. The teeth were used for spectroscopic measurements without any treatment. Synthetic hydroxyapatite in powder form was obtained from Sigma-Aldrich Inc. (St. Louis, Mo., USA) and used for confirmation of Raman spectral peak assignments of hydroxyapatite within tooth enamel.

2.2 Optical Coherence Tomography

Optical coherence tomography image slices were acquired on an OCT-2000 system with software Revision A (Humphrey Systems, Dublin, Calif., USA) and equipped with a superluminescent diode source. The source has a central wavelength of 850 nm and the laser spot size is 10-20 µm. The optical power at the sample was 750 µW for all image sets. Both the axial and transverse resolutions were 10-20 µm. The OCT-2000 system has an x-y galvanometer pair for beam steering and an integrated camera for sample viewing during data collection. For image acquisition, the galvanometer pair was limited to straight-line collection only. The shortest lateral scan length (~2.0 mm) of the system was used to provide images of high pixel density. The scan rate was 100 A-scans/second. For these ex vivo studies, tooth samples were imaged in an upright position by affixing the apical root portion of the tooth to the microscope slide using dental rope wax. The samples were imaged using a free-space coupled arrangement. The laser line was focused to the thinnest line on the sample image and during acquisition, the polarization was matched to the sample in order to optimize the OCT signal strength. OCT data were exported into MATLAB (The Mathworks Inc., Natick, Mass., USA) and interpolated using a bilinear filter method within MATLAB to generate false-colour images. The scan length was corrected for non-ophthalmologic uses of the system by imaging a linear scale. The depth distance was corrected by dividing the depth obtained from the system (assuming imaging in air) by a value of 1.6, the refractive index of tooth enamel.[40]

2.3 Raman Microspectroscopy and Fibre-Optic Raman Spectroscopy

Raman spectra were acquired on a LabRamHR confocal Raman microspectrometer (Jobin-Yvon Horiba, Edison, N.J., USA) operating with near-infrared (NIR) laser excitation at 830 nm (Lynx series TEC 100 diode laser, Sacher Lasertechnik GmbH, Marburg, Germany), (FIG. 1). In brief, the Raman microspectrometer consists of an Olympus BX41 microscope equipped with a motorized XYZ stage, a spectrograph with 300 lines/mm grating and an air-cooled CCD detector optimized for the NIR region. Spectra were also acquired using a fibre-optic Raman probe (830 nm excitation, InPhotonics, Mass., USA) that was interfaced to the LabRamHR spectrometer. Laser powers at the sample were 24 mW, 39 mW, 54 mW, 48 mW and 52 mW under ×100 (Olympus LMPlan IR), ×50 (Olympus MPlan), ×10 (Nikon), ×5 (Leica HC PL Fluotar) microscope objectives and fibre-optic probe, respectively. For microspectroscopy, the confocal hole size was set at 800 µm and the slit size at 100 µm. The spectral resolution was 4 $cm^{-1}$ for the spectra acquired with the microscope objectives and 7 $cm^{-1}$ for the fibre-optic probe. These values were determined using an 841 nm neon line. A polarization scrambler is placed in the Raman collection path in order to eliminate potential artifacts from polarization-sensitive components (e.g. diffraction grating) (FIG. 1). LabSpec (ver. 4.12) software accompanying the LabRamHR system was used for spectrometer control and data acquisition. For Raman microspectroscopy, the tooth surface not being studied was placed lying on a microscope slide and then secured with dental wax. Wax was applied only at the apical root to ensure no wax contamination at the surfaces of interest. Tooth surfaces to be examined were positioned approximately normal to the laser beam (FIG. 1). For fibre-optic sampling, tooth samples were positioned upright on a microscope slide and the fibre-optic probe was place at a position 5 mm away (optimal laser focus) from the tooth surface. The sampling position was optimized by a XYZ translator assembled in-house. A camera coupled with an ×10 objective lens was used for monitoring the positioning and for capturing photomicrographs of the sampled locations.

Figure 2:
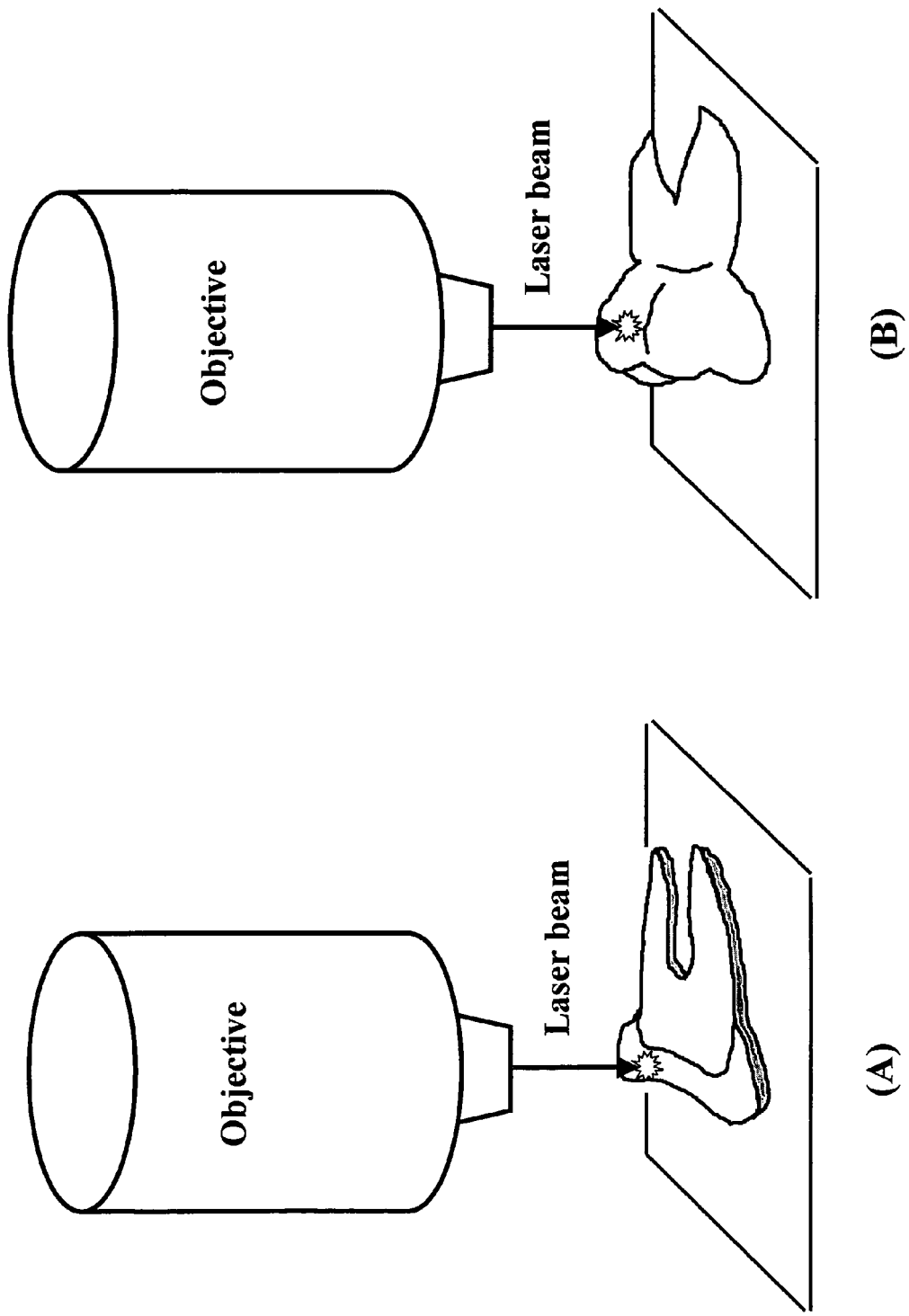
FIG. 2 is a diagrammatic representation of the two spectral acquisition configurations using (A) transverse excitation/detection on a longitudinally sectioned (crown to root direction) tooth, and (B) normal excitation/detection on an unsectioned whole tooth. Drawing illustrates the actual sample orientation under the microscope objective.

For our studies, the orientation of the enamel crystals within tooth samples were defined with respect to the laser beam as has been described by Tsuda and Arends.[36] Raman spectra obtained from the cross-sectioned surface of longitudinally sectioned (i.e. crown to root direction) tooth samples were defined as acquired in a transverse excitation/detection mode (FIG. 2A). Raman spectra recorded from un-sectioned whole tooth were defined as acquired in a normal excitation/detection mode (FIG. 2B). Spectra were measured using 30 sec acquisition time with 15 accumulations for the ×5 objective or 15 sec acquisition time with 15 accumulations for the other objectives and the fibre-optic probe in order to generate spectra of good signal to noise ratios. For point mapping experiments using the ×10 objective, the laser spot size was about 37×25 µm$^2$. Spectra were acquired at 140 µm steps along the x-axis and 113 µm steps along the y-axis resulting in a 10×10 array map covering an area of 1260×1017 µm$^2$.

Polarized Raman microspectroscopic measurements of tooth samples were acquired by placing a NIR (780-1250 nm range) linear polarizer (Melles Griot, Irvine, Calif.) in the laser excitation path after the radiation exits the laser head (FIG. 1) to obtain linearly polarized light from the originally scrambled laser polarization (Lynx series TEC 100, Sacher Lasertechnik). One set of measurements was acquired with the linear polarizer in one orientation and a subsequent set of measurements was acquired with the linear polarizer rotated 90° such that the second polarization direction is orthogonal to the first polarization direction. All other measurement conditions (e.g. optics, sample orientation, etc.) were left unchanged between the two measurement sets. Similar to the other non-polarized measurements, a polarization scrambler is placed in the Raman collection path in order to eliminate potential artifacts from polarization-sensitive components.

2.4 Raman Spectroscopic Data Analysis

Figure 3:
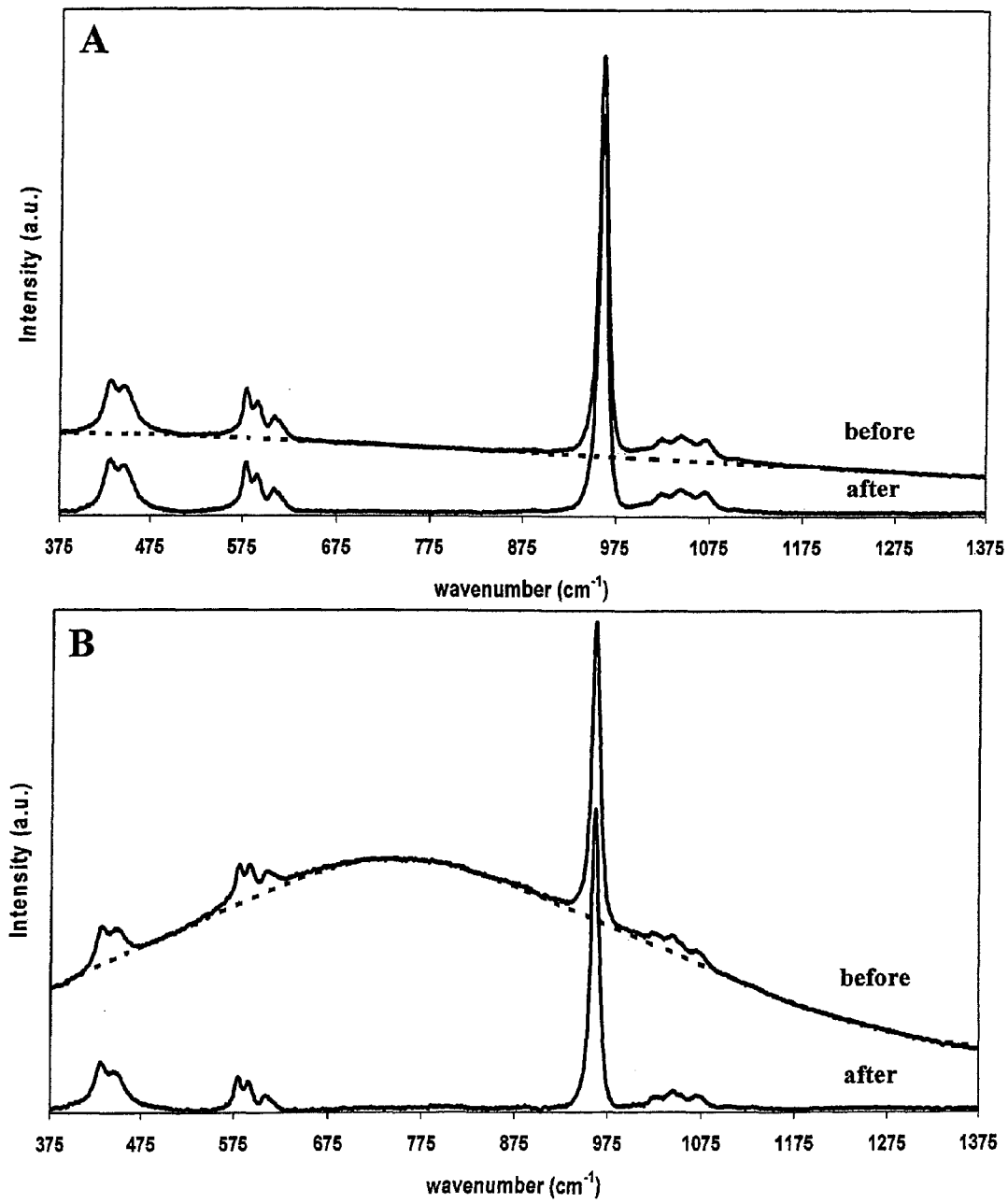
FIG. 3 is a representative Raman spectra illustrating the background fluorescence acquired from (A) the majority of sound and carious dental enamel and (B) from a few number of carious sites. For both panels, the upper solid traces illustrate the original spectrum. The dashed traces are the $6^{th}$ order polynomial fits that were used for correction and the lower solid traces are the results after subtracting the polynomial fits of the background fluorescence.

Background Raman spectrum, acquired with no sample in place and with all other experimental conditions unchanged, was subtracted from sample spectra to correct for background signal arising from optical elements in the laser path. The spectrum of a luminescent green glass reference, calibrated previously with a NIST traceable reference tungsten halogen lamp (The Eppley Laboratory, Inc., Newport, R.I., USA) of known temperature, was used to correct the sample spectra for the instrument response function.[41,43] The majority of the Raman spectra (sound enamel and carious enamel) acquired contained a minor sloping baseline as the background (FIG. 3A). A few spectra of carious enamel contained a large background fluorescence (FIG. 3B). For semi-quantitative spectral analyses and mapping experiments, the spectra were first baseline corrected using a $6^{th}$ order polynomial fit through the spectra at 375 cm$^{-1}$, 512 cm$^{-1}$, 700 cm$^{-1}$, 840 cm$^{-1}$, 1200 cm$^{-1}$ and 1400 cm$^{-1}$. FIG. 3 illustrates representative spectra before and after the backgrounds were removed by subtracting the fit of the $6^{th}$ order polynomial. The corrected spectra were then normalized to the 959 cm$^{-1}$ peak. Peak ratios were determined by taking the intensities of the various Raman bands of interest. In a similar approach, an intensity ratio map was generated from the mapping data. The resulting Raman map presented was smoothed using the bilinear interpolation method for 2-dimensional data in MATLAB.

Figure 4:
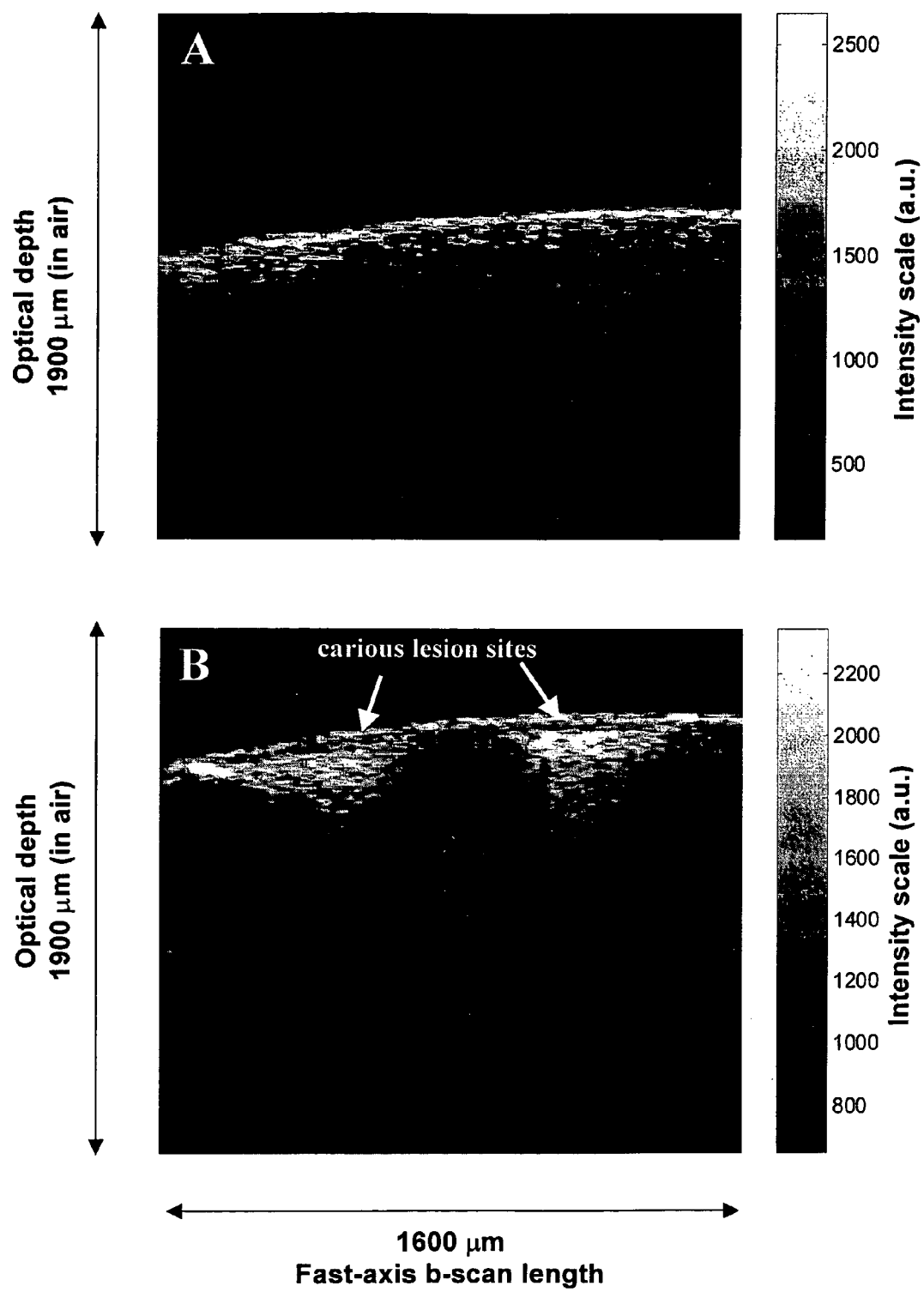
FIG. 4 is a representative false-colour OCT images of lateral scan length as a function of depth from (A) sound enamel tooth surface (minimum light back scattering with depth) and (B) carious enamel surface containing two lesions (significant light back scattering). The carious lesion sites are indicated with the arrows.

FIG. 4 shows representative false-colour OCT images obtained from a sound tooth and a tooth surface containing two clinically confirmed incipient lesions also known as white spots. The images present the lateral scan position versus the imaging depth with higher intensity correlating with greater light back-scattering. In the image of the sound tooth (FIG. 4A), an intense light back-scattering is observed at the tooth surface. This represents the scattering of the light due to the change of refractive index as the light transitions from air to the tooth enamel surface. For the sound surface, beyond the initial first few microns, the light back-scattering rapidly decays with no further changes in intensity deeper into the enamel. This image suggests that the surface is intact with no structural defects, increased porosity or loss of mineral structure. There is no evidence of a further scattering boundary deeper into the tooth that would suggest the presence of the dentin-enamel junction (DEJ). This feature, however, has been observed by other groups performing OCT imaging of tooth.[14,16] The absence of an observable scattering boundary representing the DEJ on our images is possibly due to the large enamel thickness observed at the region sampled and the attenuation of the scattered signal as it penetrates the enamel; enamel is known to weakly scatter near-infrared light (850 nm in our studies).[40] Other OCT images acquired of the enamel closer to the cemento-enamel junction (i.e. borderline between the crown and root complex) have demonstrated the DEJ (figure not shown for brevity). Therefore, it is likely the enamel thickness that limits the observation of the DEJ in our OCT images. In contrast to the image of the sound enamel surface, the image (FIG. 4B), taken of the carious sites portrays diffuse scattering in two triangular-shaped zones immediately below the surface areas. Once again there is intense light back-scattering at the tooth surface indicating that the incipient lesions have intact surfaces. The diffuse scattering intensity in the region below the surface is due to the occurrence of multiple scattering and indicative of an area of higher porosity within an otherwise dense enamel structure. This suggests that demineralization has occurred below the intact surface as occurs with early dental caries formation. Similar imaging results were reported by Fried et al. using polarization sensitive optical coherence tomography (PS-OCT) on natural interproximal lesions.[19] Based on the OCT image, it is estimated that the deepest area of the lesions is approximately 290 µm deep. The triangular-shaped region below the surface and this depth estimation is consistent with histological studies in the literature that have shown a similar triangular-shaped lesion body with 100-250 µm depth typical of "white-spot" carious lesions.[11-13] OCT is able to provide morphological information of near-surface tissue structures and defects and is particularly sensitive to changes in refractive index as the light interacts with the sample. It is therefore a good first approach for examining tooth samples to screen for early dental caries and estimating the lesion depth. From a clinical perspective, lesion depth is useful for determining the extent of caries activity and in aiding the decision to surgically restore or promote remineralization. In addition, the depth can be used to monitor remineralization and to evaluate the arrest of further caries progression.

3.2 Raman Microspectroscopy of Sound and Carious Enamel

Following the identification of a possible carious lesion by OCT, false-positive results can be reduced by confirming the presence of caries using Raman spectroscopic characterization.

Figure 5:
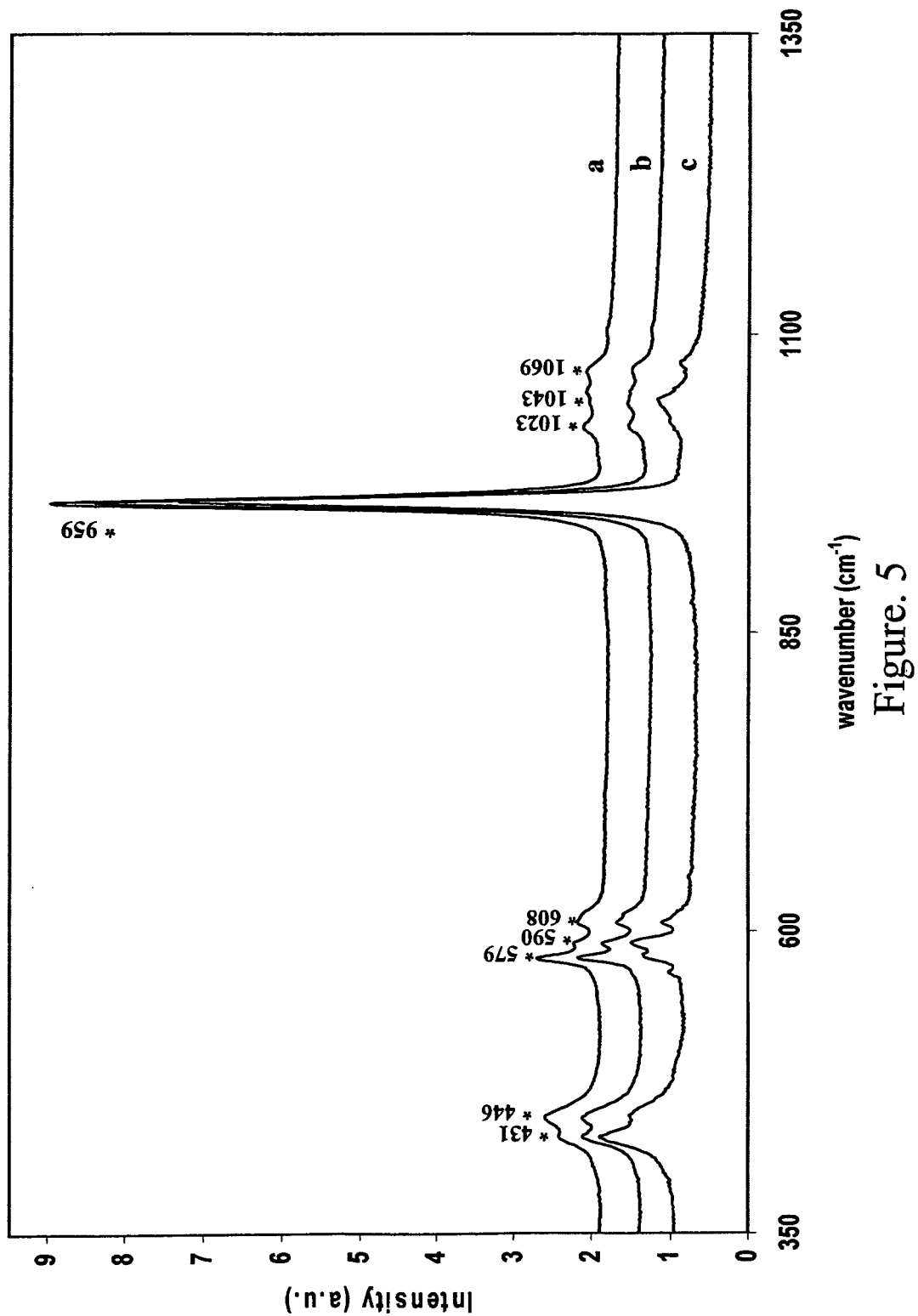
FIG. 5 is a representative microspectroscopic Raman spectra of (a) sound human enamel, (b) carious human tooth enamel and (c) synthetic hydroxyapatite (OHAp) acquired with ×10 objective. Spectra are offset for clarity. The asterisks indicate peak positions. See discussion for further details.

FIG. 5 illustrates representative Raman spectra, obtained with an ×10 objective lens, of sound enamel and carious enamel, both from un-sectioned whole teeth, and of synthetic hydroxyapatite (OHAp). The major band positions and tentative assignments of enamel and OHAp spectra are summarized in Table 1 and are compared with those previously reported. Our Raman spectra show good agreement with the literature values in terms of the respective Raman shifts. An examination of the Raman spectra from sound and carious enamel revealed differences in the relative band intensities of various Raman peaks, however, no new bands, band shifts, nor disappearance of bands were evident. The symmetric stretching vibration (vi mode) of phosphate ($PO_4^{3-}$) at 959 $cm^{-1}$ dominates both sound and carious enamel spectra. The peak position is characteristic of carbonated biological apatite found in bone, dentin and enamel.[21,24,29] A similar peak in the spectrum of synthetic hydroxyapatite has a peak maximum at 962 $cm^{-1}$. The higher Raman shift of this peak indicates a higher crystallinity of the synthetic hydroxyapatite as compared to carbonated hydroxyapatite. In carbonated hydroxyapatite, $CO_3^{2-}$ has been known to substitute $PO_4^{3-}$ yielding type-B carbonated hydroxyapatite; in type-A $CO_3^{2-}$ substitution, the $OH^-$ is replaced in the hydroxyapatite crystal.[45] The incorporation of $CO_3^2$ into the hydroxyapatite crystal deforms the crystal structure causing a decrease in crystallinity. There was no obvious change in the full width at half maximum (FWHM) of the 959 $cm^{-1}$ peak between sound and carious enamel spectra. The FWHM is ~10.0+/-0.24 $cm^{-1}$ and corresponds to earlier studies that have examined the FWHM of enamel.[46] Studies involving infrared absorption and Raman studies have reported the broadening of this peak upon incorporation of $CO_3^2$ (type-B) into synthetic hydroxyapatite.[47,48] Since an early event of demineralization is the dissolution of $CO_3^{2-}$ by acid attack,[49] one might expect the spectra of carious lesions to have an increased $\Box_1$ $PO_4^{3-}$ Raman shift and decreased peak width compared to spectra of sound enamel. Both of these features would be indicative of increased hydroxyapatite crystallinity. Such changes were not observed. Our studies involve biological hydroxyapatite, however, the crystallinity differences reported in the literature were from studies involving synthetic hydroxyapatite crystals.

An examination of the 1069 $cm^{-1}$ peak assigned to both $PO_4^{3-}$ and type-B $CO_3^{2-}$ of apatite also show no obvious changes between sound and carious enamel despite the loss of carbonate with demineralization. Chemical analyses of different histological zones of the enamel lesion showed a carbonate level of 1-2% (wt/wt) in the lesion body compared to an average of 2% (wt/wt) in the outside layers of sound enamel.[50,51] It is not surprising that Raman spectroscopy is unable to detect the difference at this low concentration level. Spectral analyses is further complicated by the fact that the peak at 1069 $cm^{-1}$ is a combination of $PO_4^{3-3}$ and type-B $CO_3^{2-}$ vibrations.

In spite of these findings, changes are visibly observed with the formation of white spot lesions. There should then be some underlying biochemical or structural alterations giving rise to the clinically detected differences. The various other phosphate peaks were therefore examined more closely. In particular, peak intensity ratios were determined to be a better method for interpreting such spectroscopic data. This approach was chosen since Raman spectroscopy is known for its sensitivity toward sampling geometry such as laser focusing distance, sampling angles and the topography of the sample surface. This is especially true for (confocal) Raman microspectroscopy where the sampling volume is very small and any minor variations in sampling condition can alter the collection efficiency, thus affecting the signal intensity.

Figure 6:
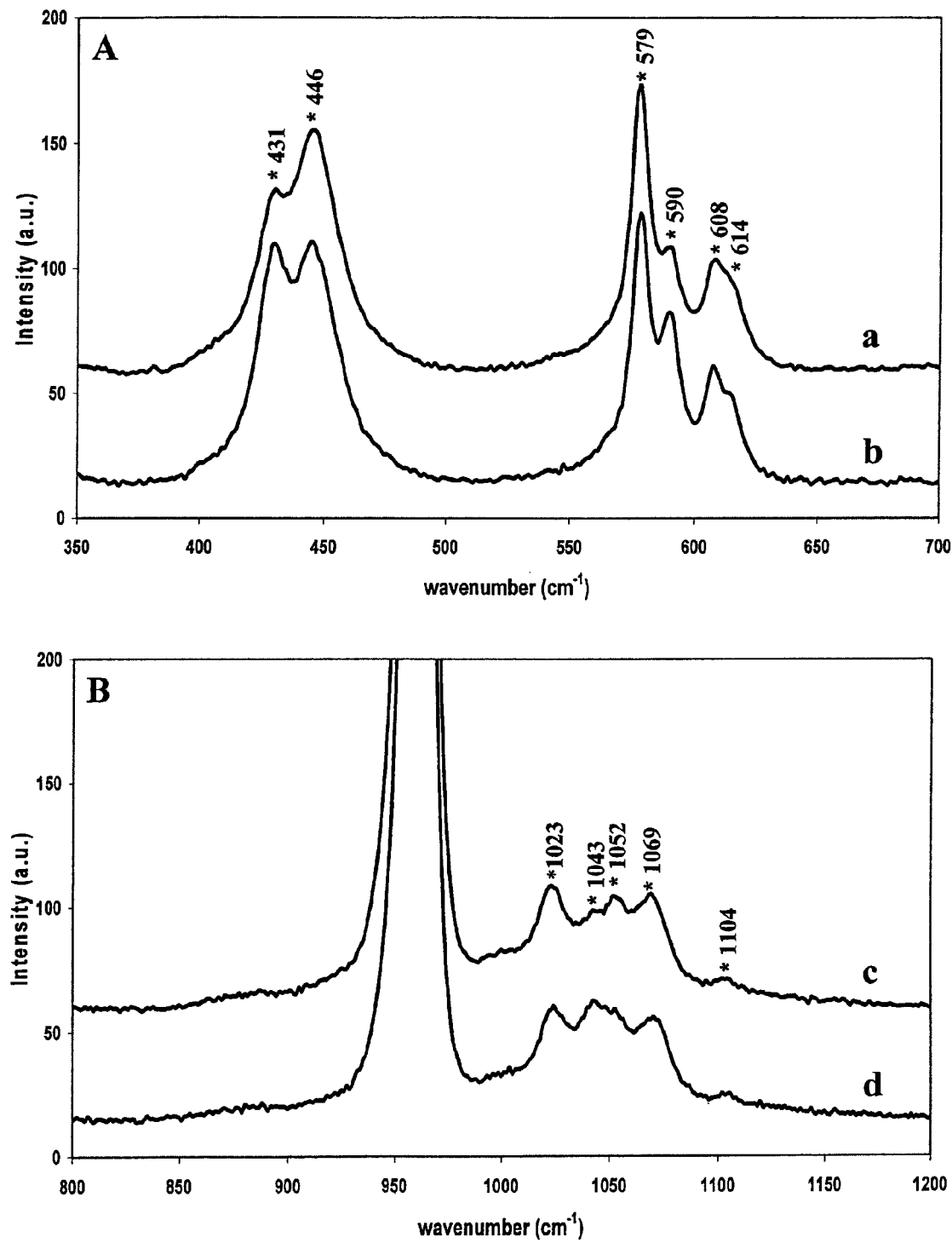
FIG. 6 is a representative microspectroscopic Raman spectra in the region of (A) 350-700 $cm^{-1}$ and (B) 800-1200 $cm^{-1}$ of sound enamel (a & c) and carious enamel (b & d). Spectra were acquired with ×10 objective and offset for clarity. The asterisks indicate peak positions.
Figure 7:
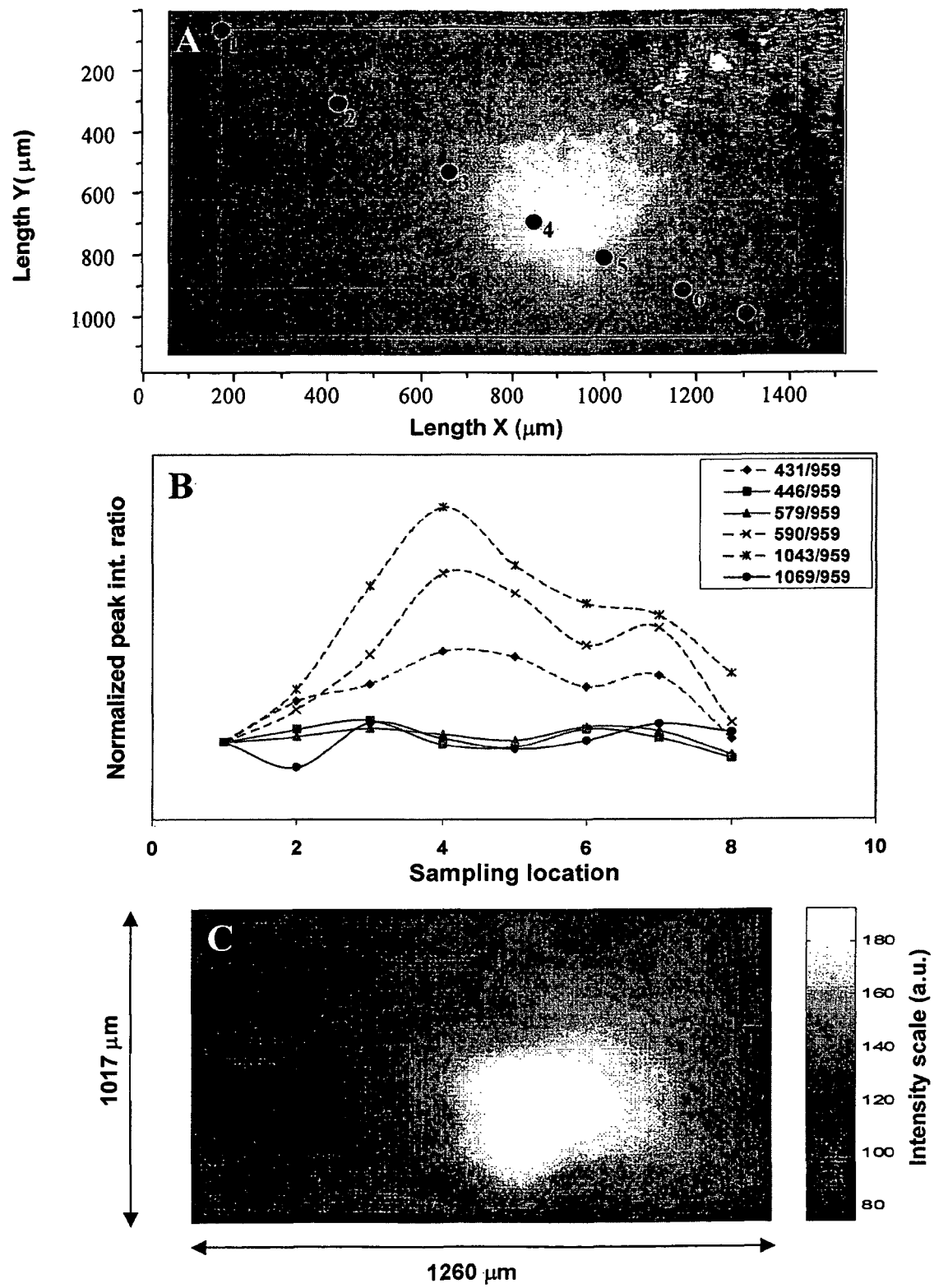
FIG. 7 is a (A) photomicrograph of a human enamel tooth surface containing a carious lesion (white area). The shaded dots represent the sampling locations of the spectra acquired across the surface and used to generate (B) the peak intensity ratio plot of various phosphate peaks relative to the 959 $cm^{-1}$ peak. (C) Raman 2-D image map of the same lesion area illustrated in (A). The smoothed Raman spectral imaging map was generated using the intensity ratios of the 1043 $cm^{-1}$/959 $cm^{-1}$ peaks and plotted as a function of the 10×10 point mapping array. (See Materials and Methods section for details).

FIG. 6 shows representative Raman spectra of sound and carious enamel in the regions of 350-700 $cm^{-1}$ (FIG. 6A) and 800-1200 $cm^{-1}$ (FIG. 6B). Symmetric bending vibrations ($v_2$ mode) of $PO_4^{3-}$ give rise to two major peaks at 431 $cm^{-1}$ and 446 $cm^{-1}$. In the sound enamel spectrum, the 446 $cm^{-1}$ peak has a greater intensity than the 431 $cm^{-1}$ peak. These two bands are also present in the caries spectra, however, their relative intensities are reversed with the 431 $cm^{-1}$ peak intensity greater than the 446 $cm^{-1}$ peak. A series of bands at 579 $cm^{-1}$, 590 $cm^{-1}$, 608 $cm^{-1}$ and 614 $cm^{-1}$ (shoulder band) are assigned to asymmetric bending vibrations ($v_4$ mode) of $PO_4^{3-}$. The band pair at 579 $cm^{-1}$ and 590 $cm^{-1}$ shows an intensity profile change similar to that observed for the $v_2$ mode with the 590 $cm^{-1}$ band of greater intensity in the caries spectrum but weaker intensity in the sound enamel spectrum. The two bands at 608 $cm^{-1}$ and 614 $cm^{-1}$ do not demonstrate obvious changes between sound and carious enamel spectra. The asymmetric stretching vibration ($v_3$ mode) of $PO_4^{-3}$ constitutes a more complicated region of the spectra (FIG. 6B). Raman bands were observed at 1023 $cm^{-1}$, 1043 $cm^{-1}$, 1052 $cm^{-1}$ and 1069 $cm^{-1}$. The intensity of the 1043 $cm^{-1}$ band increases noticeably in the caries spectrum whereas the other three bands do not show prominent intensity variations. The numerous tooth samples examined showed various degrees of spectral change between sound and carious sites, however, the bands at 431 $cm^{-1}$, 590 $cm^{-1}$ and 1043 $cm^{-1}$ showed consistent characteristic differences. These changes are highlighted in FIG. 7B where the intensity ratios of various bands relative to the 959 $cm^{-1}$ band are plotted against sampling locations indicated in the photomicrograph of FIG. 7A. This figure depicts an enamel surface containing a carious lesion. The carious lesion appears as a white area on the image with the marked dots representing various sampling locations. The intensity ratio plot shows enhanced 431 $cm^{-1}$, 590 $cm^{-1}$ and 1043 $cm^{-1}$ bands relative to the 959 $cm^{-1}$ band at the carious lesion whereas the other bands do not show significant intensity changes. The same finding is observed in the Raman intensity ratio image map based upon the 1043 $cm^{-1}$/959 $cm^{-1}$ peaks obtained from a 10×10 point mapping study (FIG. 7C). Both the size and the location of the carious lesion on the Raman map match very well with the photomicrograph. This result further confirms the validity of the Raman bands selected for caries detection. Overall, the findings of FIG. 7 describe a method of contrasting sound and carious enamel based upon Raman signal intensity ratios of various $PO_4^{-3}$ vibrations. Hill and Petrou[39] have previously reported that carious lesions can be distinguished from sound enamel based on their Raman spectra. However their method was not fully based on the enamel's intrinsic Raman signal but rather on the level of the luminescence background upon illumination with 785 nm laser excitation. For the most part, our studies using laser excitation further to the near-infrared region (830 nm) did not show any significant background luminescence. A similar reduction of background fluorescence was also apparent in spectra acquired by Hill and Petrou in an earlier study using 1064 nm laser excitation.[38] Therein, the study focused on the 960 $cm^{-1}$ peak as well as the 930 $cm^{-1}$ and 1900 $cm^{-1}$ peak intensities for evaluation of the luminescence background.

Figure 8:
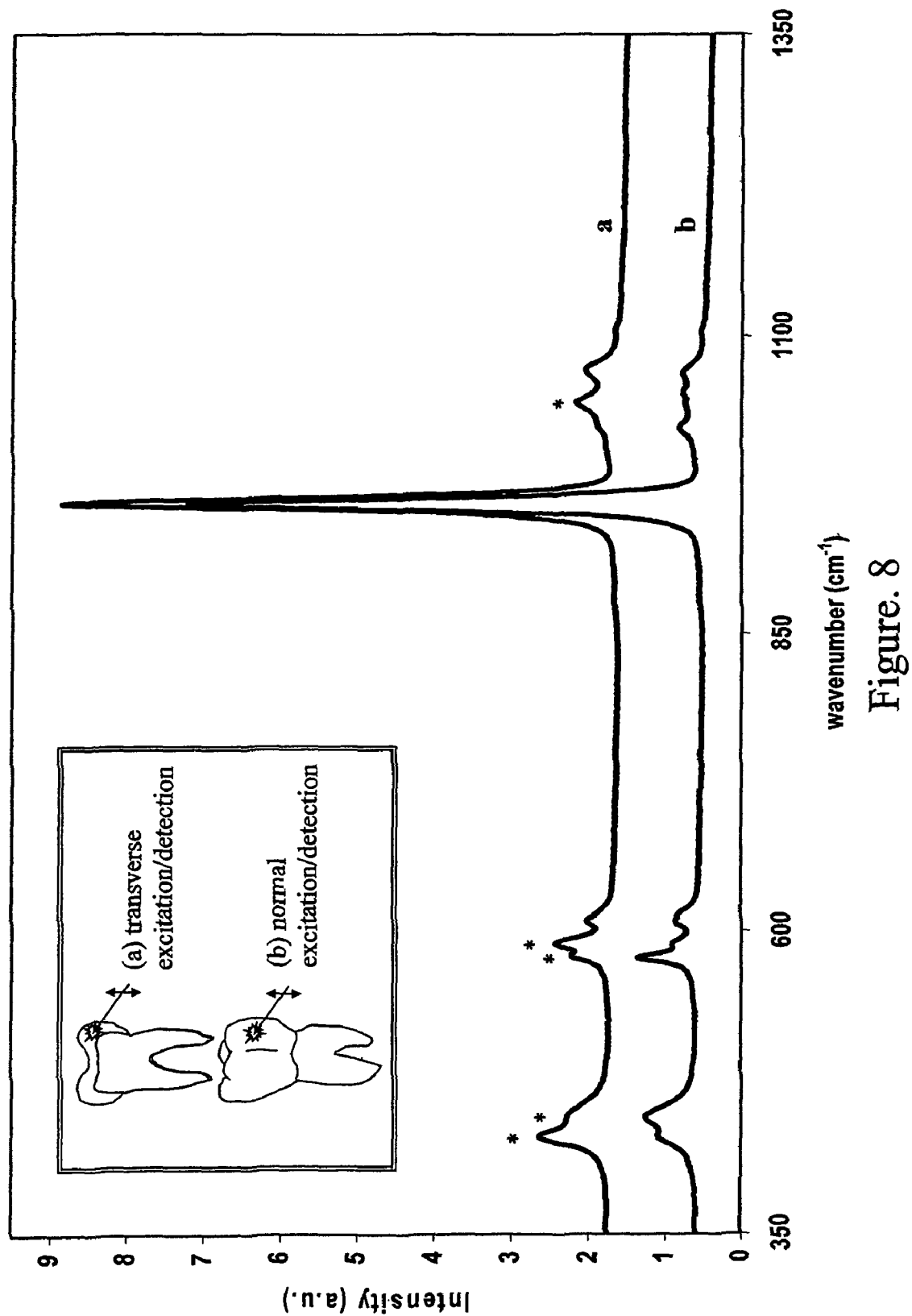
FIG. 8 is a representative microspectroscopic Raman spectra of human tooth enamel using (a) transverse exc./det. configuration and (b) normal exc./det. sampling mode configuration. Measurements were acquired with a ×10 objective. Peaks highlighted with asterisks show major intensity differences between the two sampling modes. Insert: schematic illustrations of transverse (sectioned tooth) and normal (whole tooth) exc./det. sampling arrangements. Laser beam is 90° to the sample's surface in both cases.

In order to determine a rationale for the characteristic intensity changes observed at 431 $cm^{-1}$, 590 $cm^{-1}$ and 1043 $cm^{-1}$ between sound and carious enamel, we compared our spectra more closely with those reported in the literature. It was noted that our Raman spectra of sound enamel from whole un-sectioned teeth did not have the same relative peak intensities as reported in the literature of sound enamel from cross-sectioned tooth samples. The difference between these studies lies in the sampling configuration in which Raman spectra were acquired. Representative Raman microspectroscopic data of sound tooth enamel measured using two different sampling geometries are shown in FIG. 8. The upper spectrum was acquired on a longitudinally sectioned tooth sample and known as a transverse excitation/detection (exc./det.) mode whereas the lower spectrum was acquired on an un-sectioned whole tooth termed the normal exc./det. mode. The transverse and the normal sampling arrangements are demonstrated in FIG. 2 and insert in FIG. 8. These two spectra show differences in several band intensities, which are highlighted with asterisks. The transverse spectrum differs from the normal spectrum with relatively higher Raman signal intensities at 431, 590 and 1043 cm$^{-1}$. These same intensity differences were also observed between sound enamel spectra and carious enamel spectra when measured using a normal exc./det. configuration. The spectrum of carious enamel measured in the normal exc./det. configuration is an intermediate between the spectra of sound enamel measured with the two sampling geometries, transverse verses normal. Considering that the biochemical composition does not change when the sampling arrangement has changed and given that the Raman signal is sensitive to both the (bio)chemical composition and structure of the sample, it is believed that the spectral differences between the two measurement configurations and between sound and carious enamel arise from structural characteristics of the enamel rods[36,37]. Tooth histology indicates that hydroxyapatite crystals are bundled into long rods with ~4-7 □m diameter.[49,52] A small portion of the enamel rods are randomly oriented but the majority are highly oriented within the enamel layer with their c-axis (the longer axis) approximately perpendicular to the natural tooth surface.[36,49] This orientation is observed on the entire crown surface, i.e. at the top (occlusal or incisal surface) and at the sides (proximal surfaces) of the tooth crown.[49] Previous polarized Raman studies have indicated that changes in the spectral profile of enamel crystals reflect changes in the c-axis orientation.[36,37]

Figure 9:
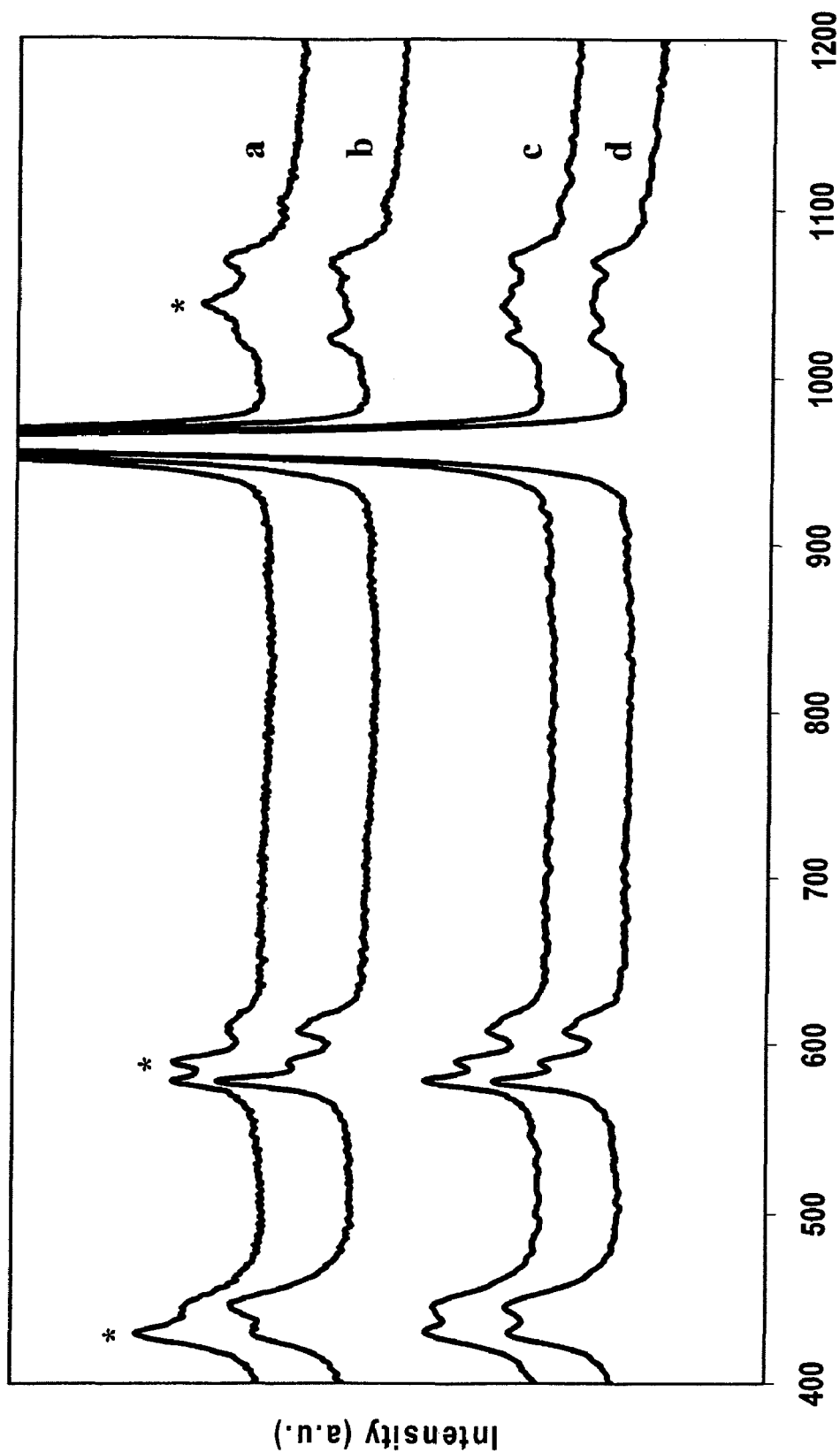
FIG. 9 is a representative polarized Raman spectra of sound enamel (a & b) and carious enamel (c & d) acquired with the linear polarizer in one polarization direction (a & c) and the orthogonal polarization orientation (b & d). The asterisks highlight peak positions.

Therefore, we propose that the spectral differences observed between sound and carious enamel are due to the hydroxyapatite crystallite orientation in the enamel. The demineralization process of caries formation results in changes of the enamel crystallite morphology or a loss of preferred enamel crystallite orientation which is reflected in the Raman spectrum. Polarized Raman spectroscopy has been shown to be useful in determining the enamel crystallite orientation and the structural symmetry.[36,37] Preliminary polarized Raman studies on sound and carious enamel were performed to explore the hypothesis that demineralization results in alterations in enamel crystal orientation. FIG. 9 shows representative polarized Raman spectra of sound enamel (traces a & b) and carious enamel (traces c & d) acquired with the linear polarizer at one polarization orientation (traces a & c) compared to the orthogonal polarization orientation (traces b & d). It is observed that the intensity of the phosphate $v_2$ (431 cm$^{-1}$), $v_4$ (590 cm$^{-1}$) and $v_3$ (1043 cm$^{-1}$) peaks of sound enamel alters with the change in the polarization direction of the laser excitation. These peaks are therefore sensitive to the change in laser polarization suggesting that sound enamel is optically anisotropic. In contrast, these same peaks in Raman spectra of carious lesions do not change significantly when the laser polarization direction is rotated. Therefore the peaks are much less sensitive to the changes in laser polarization and this indicates that carious enamel is optically isotropic due to scrambling of the hydroxyapatite crystallite orientation upon demineralization. These observations support the suggestion that crystallite structural orientation changes are responsible for the spectral changes observed between sound and carious enamel.

3.3 Fibre-Optic Raman Spectroscopy of Sound and Carious Enamel

Figure 10:
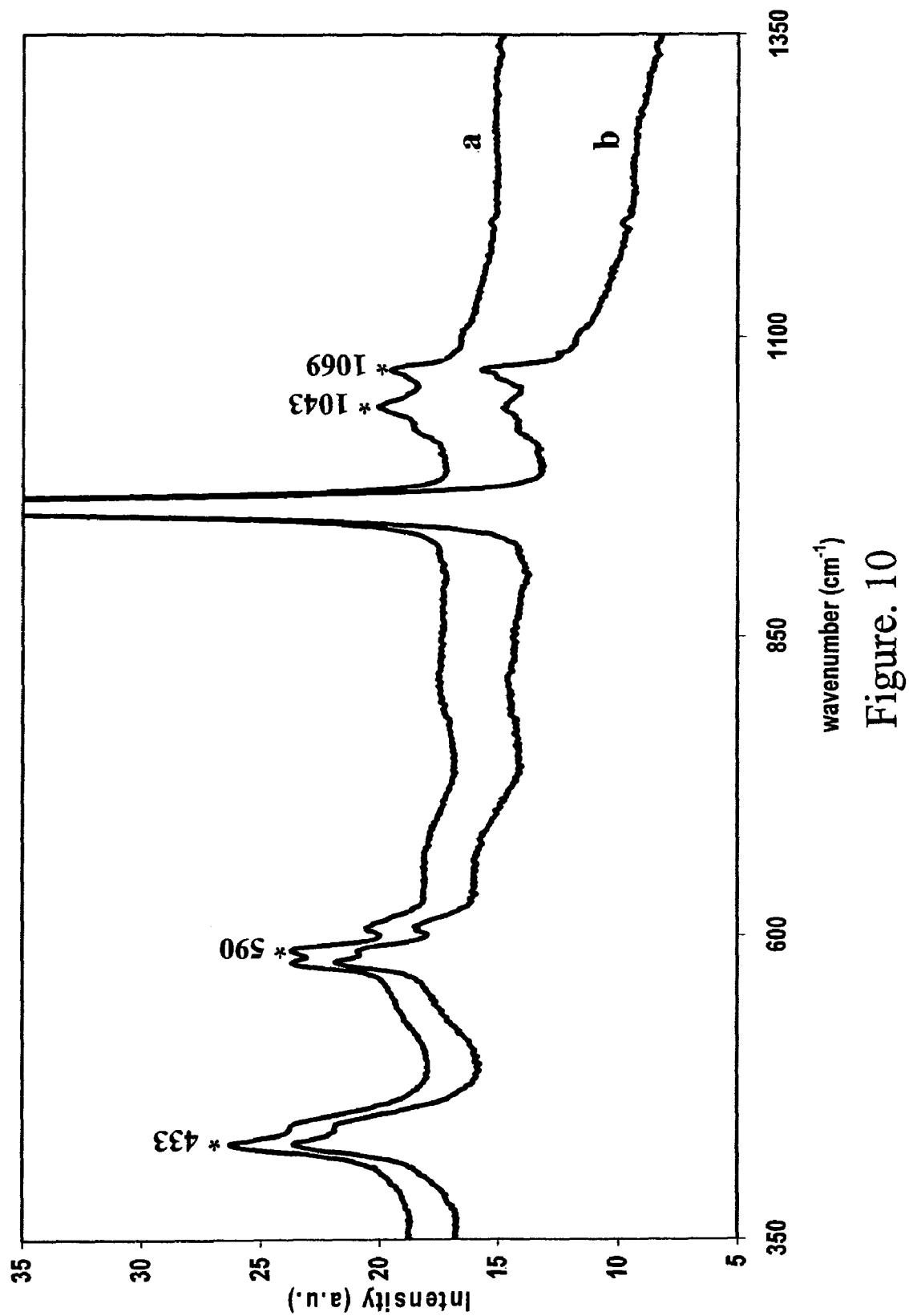
FIG. 10 is a representative fibre-optic Raman spectra (not corrected for luminescence background) of (a) carious enamel and (b) sound enamel acquired with an InPhotonics Raman probe for 830 nm laser excitation. Spectra were normalized to the 959 $cm^{-1}$ peak and were offset for clarity.

So far, we have demonstrated that carious enamel can be distinguished from sound enamel at the microspectroscopic level using the intensity changes of the hydroxyapatite Raman bands. We proceeded to investigate the suitability of a fibre-optic Raman probe for caries detection. Representative fibre-optic Raman spectra (not corrected for background fluorescence) of carious and sound tooth are illustrated in FIG. 10 with band assignments listed in Table 1. The major bands identified in spectra acquired with the fibre-optic probe correspond well to those observed from microspectroscopy. The overall spectral pattern of the fibre probe spectra resembles that of the microspectroscopic spectra. However, a slightly higher level of background luminescence is observed with the spectra possessing lower spectral resolution (~7 cm$^{-1}$) as shown by the unresolved peak at 1053 cm$^{-1}$. Comparing sound enamel and carious enamel spectra, similar increases in Raman peak intensities at 433 cm$^{-1}$, 590 cm$^{-1}$ and 1043 cm$^{-1}$ are detected using a fibre-optic probe as with Raman microspectroscopy. The degree of changes is however less than that detected with the microscope objective and is likely the result of a larger sampling depth obtained by the fibre probe. The larger sampling depth obtained with the fibre probe indicates that the region beyond the caries lesion and into the healthy enamel layer was possibly measured in the Raman spectra. As such, any spectral contribution from the carious lesion is gradually diminished in the overall spectrum in turn resulting in slightly decreased degree of spectral discrimination between sound and carious enamel.

Figure 11:
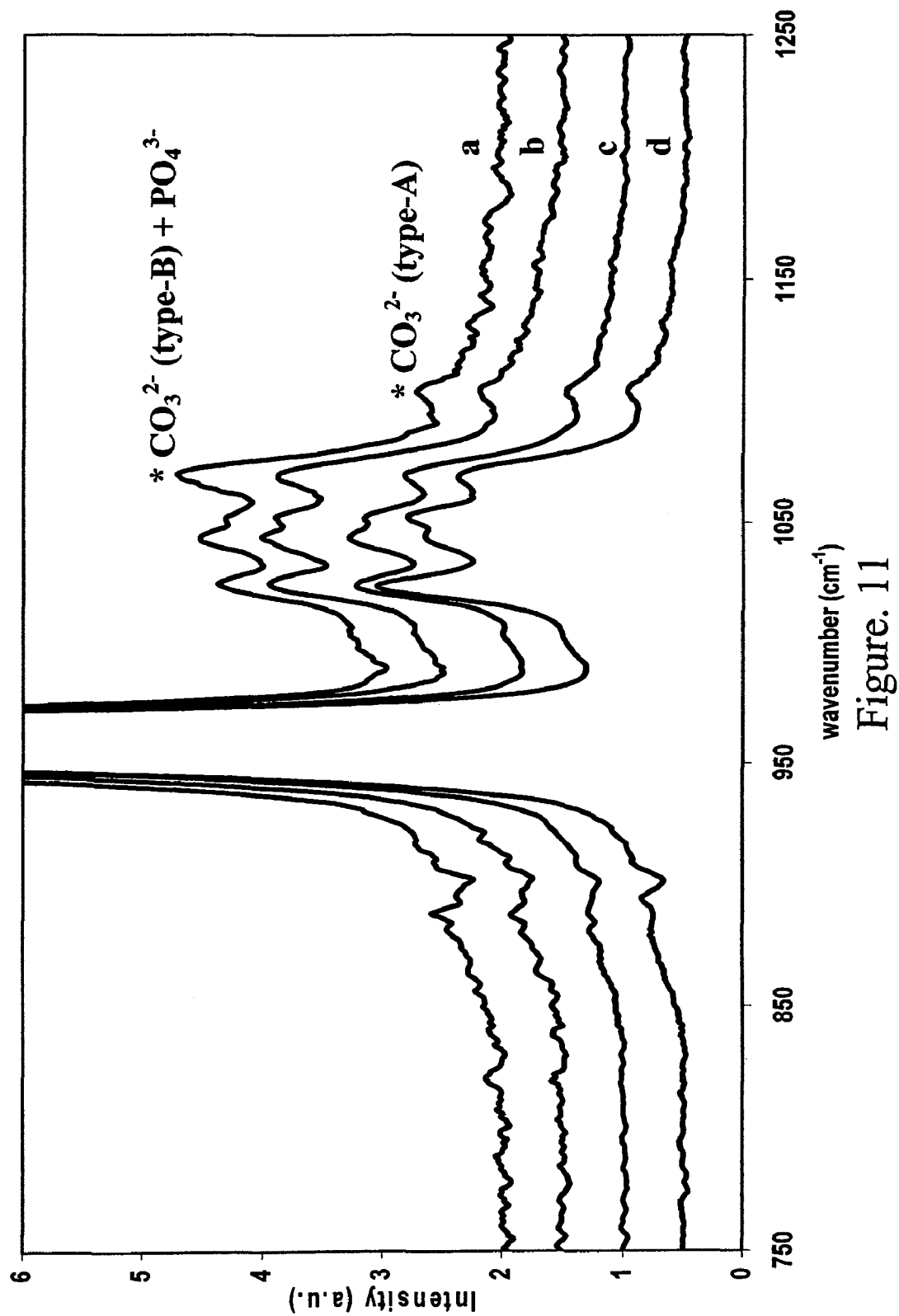
FIG. 11 is a representative Raman microspectroscopic spectra in the 750-1200 $cm^{-1}$ region of sound enamel measured with (a) ×5, (b) ×10, (c) ×50 and (d) ×100 microscope objectives.

The greater sampling depth of the fibre-optic probe is also supported by the observation of a more intense band at 1070 cm$^{-1}$ for fibre probe spectra compared to spectra acquired by microscopy. As mentioned earlier, this peak arises from $PO_4^{3-}$ and type-B $CO_3^{2-}$ of hydroxyapatite. Carbonate content is known to increase within the tooth progressing from the enamel surface to the DEJ where it reaches its maximum.[29,49,53] In FIG. 11, we present Raman microspectroscopy spectra measured of sound whole tooth enamel with a series of increasing magnification microscope objective (×5, ×10, ×50, ×100) with increasing numerical apertures and therefore decreasing sampling volumes. Focusing on the 750-1200 cm$^{-1}$ region, we observe that the $CO_3^{2-}$ intensity at 1069 cm$^{-1}$ is indeed decreasing continuously from the ×5 spectrum to the ×100 spectrum. The results with a low magnification objective and the fibre-optic data are in agreement with the known rise in carbonate content deeper into the tooth crown.

The larger sampling depth of the Raman fibre probe resulted in a slight decrease in the spectral differences between sound and carious enamel. For this reason then, it is desirable to use a fibre probe with pseudo-confocal arrangement where the measurement volume more closely approximates that of the ×10 microscope objective. With such sampling depths, healthy and early decaying enamel can readily be distinguished. Although useful for characterizing and confirming demineralization, using such a Raman probe alone would not be practical for screening in order to locate possible carious sites. The small sampling of Raman point spectroscopy would result in a greater chance of missing the lesion. For this reason, it is beneficial to couple OCT imaging with Raman spectroscopy. For the purposes of detecting suspicious carious sites, OCT would be useful for rapidly screening larger areas than that interrogated with the Raman probe. The region covered by the current OCT system is approximately 1 mm across. Although a small range, this is sufficient to probe the approximately 2 mm×2 mm area found below (gingival to) the contact points of adjacent teeth where such interproximal caries develop. OCT can therefore be used to sweep across this region to rapidly identify possible early carious sites as well as to determine the lesion depth. Based upon OCT morphological guidance, Raman spectroscopy can then be used to examine the suspected lesion to provide biochemical information. For example, a Raman probe can be used to sample various points along the OCT imaging line. Then based upon the ratios of the various Raman peaks, it can be determined rapidly whether the region exhibits spectral properties indicative of (early) carious enamel and distinguished from sound enamel. The Raman data therefore confirms the scattering aberration detected by OCT to be a carious lesion. The combination of both techniques overcomes the limitation of using each technique alone leading to results of better sensitivity and specificity.

Figure 12:
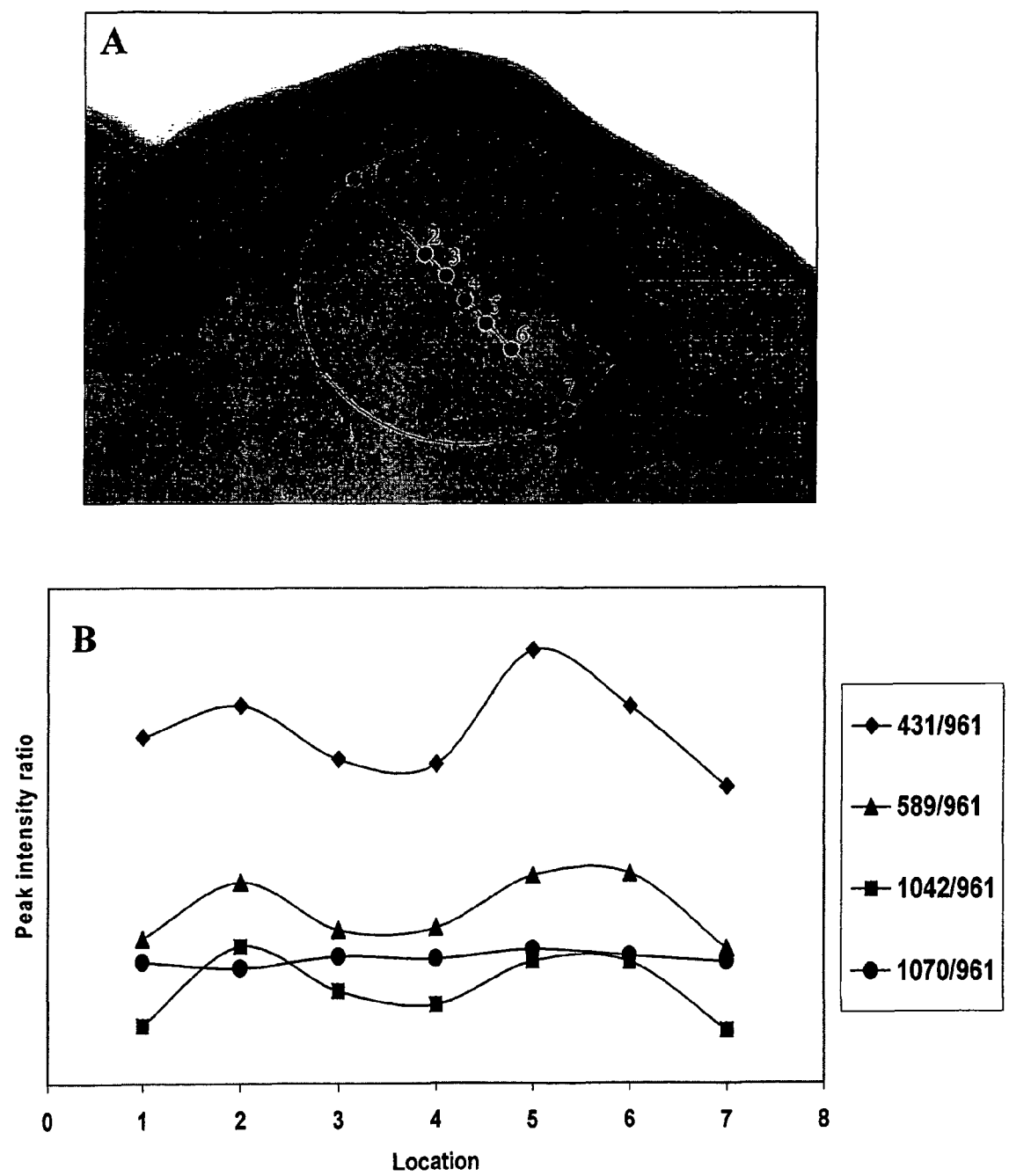
FIG. 12 is a (A) photomicrograph of a tooth surface containing two carious lesions (white areas). Shaded dots represent actual Raman sampling locations with a fibre-optic Raman probe. (B) Intensity ratio plot of various Raman peaks (431 $cm^{-1}$, 589 $cm^{-1}$, 1042 $cm^{-1}$ and 1070 $cm^{-1}$) relative to the 961 $cm^{-1}$ peak corresponding to the sampling locations shown in (A).

In order to examine the reproducibility of fibre-optic Raman spectroscopy for caries characterization, multiple-point measurements were acquired along a line on a tooth surface containing two carious lesions. The same lesion was previously examined by OCT and shown in FIG. 4B. FIG. 12A highlights the points sampled (shaded dots shown on the image in a linear fashion) and FIG. 12B shows the respective intensity ratio of various peaks relative to the $v_1$ $PO_4^{3-}$ peak at each sampling location. The increased intensity ratio correlates well with the locations of the carious lesions, as previously observed with the microspectroscopic study (see FIG. 7B). These findings also correspond well with the OCT imaging where regions of carious lesions demonstrated increased light back-scattering intensity. Therefore, the spectroscopic contrast between the carious and sound enamel present in the microscopic spectra is largely preserved in the fibre-optic measurements. This observation supports the possibility of transferring this technology from a lab bench study to a clinical application.

Our studies have demonstrated that optical coherence tomographic imaging of incipient dental caries results in increased light back-scattering intensity in a triangular-shaped region below the enamel surface suggestive of demineralization during caries development. The OCT images also provide an estimate of the carious lesion depth. Furthermore, we have shown that near-IR Raman microspectroscopy and fibre-optic Raman spectroscopy are useful for characterizing early dental caries. Sound enamel can be distinguished from carious enamel based on changes of various Raman band intensities arising from $PO_4^{-3}$ of hydroxyapatite within mineralized tissue. The local ultrastructural and morphological changes induced by the de-/re-mineralization activities during caries development give rise to the spectral changes observed. In particular, the loss of the original symmetry and/or orientation of the enamel apatite crystallites within the demineralized zone as a result of mineral dissolution may be responsible for the observed changes. Preliminary polarized Raman spectroscopic studies have provided evidence to support this hypothesis.

Good correlation has been demonstrated between the OCT images with Raman spectral and imaging data for caries detection and characterization. At lesion sites where OCT reveals deeper light penetration and stronger scattering indicative of a highly porous structure, Raman spectroscopic changes characteristic of enamel structural alterations were also observed to confirm demineralization. We have shown that by combining the strengths of both OCT and Raman spectroscopic techniques, a new optical method for early enamel caries detection can be developed. Furthermore, the use of specialized fibre-optic probes will provide improved access to the interproximal region compared to conventional diagnostic tools. The advantage of using OCT for in vivo caries detection is facilitated with a probe device. The white spot lesions described for the current studies were observed upon ex vivo visual inspection by two clinicians. Prior to extraction, the white spot lesions are at the interproximal regions. Since these lesions are not visible because they are blocked by the adjacent tooth, the lesion is often not diagnosed by the dentist. A probe that accesses the proximal surfaces would allow OCT screening for incipient caries. Merely having a visible imaging fibre to obtain a direct visual image of the interproximal region is not necessarily sufficient to detect white spot lesions. This is because the early white spot lesion is usually observed with the assistance of air-drying the tooth surface. Such lesions are more difficult to observe when wet. For the current application, OCT provides the same overall information about the presence or absence of a carious lesion regardless of a wet or air-dried surface. OCT would therefore help locate early dental caries and provide depth information, a parameter which is not available from visual inspection of intact teeth but which is important for clinical treatment decisions. Using Raman spectroscopy with OCT would furnish biochemical specificity of the presence of demineralization and confirm the results suggested by OCT. Furthermore, with Raman spectroscopy, semi-quantitative measures of the extent of demineralization can be obtained. From a clinical viewpoint, this information would be useful to the dentist in helping determine treatment strategies such as deciding to surgically restore the lesion (if at the advanced stage) or to promote remineralization and monitor the carious site over time. The non-ionizing nature of these multi-modal optical methods will also allow for frequent patient monitoring and thus improving the quality of dental health care.

Polarized Raman Spectroscopy

Characteristic changes are observed in the Raman spectra of sound teeth and teeth with carious lesions when the teeth are examined with polarized Raman spectroscopy. In particular, Raman spectra of sound teeth are sensitive to polarized light and show changes in the peak intensities especially in the Raman shift regions between 200-1200 $cm^{-1}$ (examples include, but not limited to, the regions of 200-400 $cm^{-1}$, 400-500 $cm^{-1}$, 500-600 $cm^{-1}$, 930-1000 $cm^{-1}$, and 1000-1100 $cm^{-1}$) when examined with laser light and collecting the Raman signal with orthogonal polarization directions. In contrast, carious lesions show less sensitivity to polarized light with relatively smaller and/or minimal changes of the Raman spectra observed in these regions between spectra of the two orthogonal polarized signals. The ratio of various peak regions when examined between parallel-vs. perpendicular-polarized light (i.e. depolarization ratio) can be correlated with the degree of caries activity and severity.

Raman spectra acquired from sound tooth enamel and carious tooth enamel using non-polarized microspectroscopy and fibre probe sampling revealed differences between sound and carious regions in the band intensities at 430 $cm^{-1}$, 590 $cm^{-1}$ and 1045 $cm^{-1}$ that are known to arise from phosphate ($PO_4^{3-}$) vibrations (especially $v_2$, $v_4$ and $v_3$ P-O vibrations, respectively) of the hydroxyapatite found within mineralized tissues. Such intensity variations were likely the result of structural and/or orientational changes of the hydroxyapatite upon de-mineralization. Under normal condition, the carbonated apatite crystallites in tooth enamel are arranged into bundles to form rods or prisms with their long axis perpendicular to the natural surface of the enamel. Upon de-mineralization, this preferred orientation is likely changed and presents itself in a more scrambled orientation. Since optical polarization techniques (such as polarized microscopy and polarized Raman spectroscopy) exploit properties of anisotropy to reveal information about structure/orientation and composition of material, the ordered structure of the sound enamel should be more sensitive to polarized light than a scrambled crystallite/rod structure found within the caries regions.

In our dental caries study using polarized Raman spectroscopy, the polarization of the incoming laser beam is fixed and Raman spectra were obtained by placing a polarization analyzer in the detection path with its polarization direction parallel ($\parallel$) or perpendicular ($\perp$) to the initial laser polarization. FIGS. 13 and 14 show the parallel ($\parallel$) and perpendicular ($\perp$) Raman spectra of sound and carious enamel between 200 and 1200 cm$^{-1}$, respectively. It is noted that in the sound enamel spectra, Raman peaks in the regions, 400-500 cm$^{-1}$, 550-650 cm$^{-1}$, 900-1000 cm$^{-1}$ and 1000-1100 cm$^{-1}$ show observable intensity variations upon changing the direction of the polarization analyzer. The carious enamel spectra, on the other hand, show lesser degree of intensity variation. This difference in the degree of optical anisotropy between sound and carious enamel therefore can be used for the diagnosis of early dental caries. In order to quantify this difference, we can calculate the depolarization ratio $\rho$ of the Raman band at ~960 cm$^{-1}$ (P-O symmetric stretching vibration, its actual position varies between 936 cm$^{-1}$ and 983 cm$^{-1}$ depending on structure) for both sound and carious enamel according to the following equation, $$\rho = I_{(\perp)}/I_{(\parallel)}$$

where $I_{(\perp)}$ and $I_{(\parallel)}$ are the integrated peak intensities of the 960 cm$^{-1}$ peak in orthogonally polarized Raman spectra. FIG. 15 demonstrates a statistical analysis of the experimental p values obtained for sound ($\rho_s$) and carious ($\rho_c$) enamel. It shows that the difference in $\rho$ values between sound and carious enamel is statistically significant, with P<0.01. In this case, the higher p means a more scrambled structure and presence of a carious region.

Alternatively, quantification of the anisotropic difference can also be achieved by using the following equation:

$$A = (1-\rho)/(1+2\rho) \text{ with } \rho = I_{(\perp)}/I_{(\parallel)}$$

or $$A = (I_{(\parallel)} - I_{(\perp)})/(I_{(\parallel)} + 2I_{(\perp)})$$

Where A is anisotropy or sometimes called the conventional index of orientation.

FIG. 16 shows the statistical analysis of A values of sound and carious enamel. Once again, sound enamel is statistically different from carious enamel based on the A value, with P<0.01. Contrary to the depolarization ratio ($\rho$), higher A value means higher degree of anisotropy, therefore a more ordered structure as found in sound enamel.

Not only can the $\rho$ or A values allow differentiating between sound enamel and early stage carious enamel, it also provides insight to the degree of enamel rod orientation scrambling which is directly linked to the severity of a carious lesion. Therefore, it is believed that by looking at either $\rho$ or A value, it is possible to determine the status of a suspected caries lesion and also monitor its progress over time. Furthermore, this technique can be used not only to monitor demineralization (lesion's progression) but also to monitor remineralization due to treatment strategies.

Since both non-polarized and polarized Raman demonstrate the capability of differentiating between sound and carious enamel, therefore, from an instrumentation point of view, there are at least 4 possible optical arrangements from which a practical instrument can be built upon. The first one is simply an un-polarized Raman option, which could involve but not limit to the use of optical fibers for transmission of laser and Raman signal. The second option is to use two optical polarization elements (such as polarizers/analyzers), one in the laser excitation path and the other one in the Raman detection path. The third and the fourth options are to have only one optical polarization element (such as a polarizer) placed either in the laser path or in the detection path. In our study, grating based spectrometers were used to disperse the collected Raman signal so that a full spectrum can be obtained in a single measurement. This is useful especially when more information is desired. Yet, if it is pre-determined that monitoring the intensity variation of a single Raman band, such as the one at ~960 cm$^{-1}$, is sufficient to allow differentiation between sound and carious enamel, the grating based spectrometer could be replace by a band-pass filter based system with the filter's centering wavelength identical to that of the monitored Raman band. In such case, the CCD detector can be replaced with a more simple detection system such as a photodiode detector.

Quantification Parameters

Using the depolarization ratio and/or the anisotropy index of orientation, a baseline value for healthy sound enamel can be determined. From the studies, it is clear that these values differ from those found from early demineralized white spot regions. The severity or extent of dental decay, i.e. demineralization, can therefore be determined from these parameters. For example, using the depolarization ratio of the ~960 cm-1 Raman peak, a value in the approximate range of 0.08+/−0.03 is indicative of sound enamel. In contrast, a value of the approximate range of 0.33+/−0.1 is suggestive of early dental caries formation. Very early lesions will have values closer to the value for sound enamel and more advanced intact lesions will have higher depolarization ratio values. Cavitation of the surface will yield no Raman signals due to the depth of the lesion being beyond the measuring volume of the Raman probe.

From the OCT data, the lesion depth can be measured. For an intact surface lesion, a lesion depth relative to the dentino-enamel junction (DEJ) can provide a quantitative measure. For example, non-cavitated lesions confined to the outer half of the enamel are synonymous to the dental classification of R1, lesions extending to the DEJ are R2 lesions. and lesions beyond these are involved caries with cavitated surfaces.

The Raman and OCT information is incorporated into the software and will return to the operator a visual measure in the form of colours of green for no decalcification, yellow for decalcification with intact surface and red indicating cavitation. Within the yellow region, there will be a numerical scale to indicate the depth or severity of the demineralization. This information is used by the operator to assist in determining which treatment action to pursue.

In order to monitor remineralization from the use of regimes such as fluoride treatment, visually on the OCT, it is possible to see a reduction in the lesion depth and an increase in the thickness of the surface layer (due to remineralization and hypermineralization). These provide a parameter for quantification. Also with Raman spectroscopy, quantification of remineralization can be followed/monitored by quantitating the CaF$_2$ Raman peak at ~321 cm$^{-1}$, due to the fluorapatite formation from remineralization.

Figure 17:
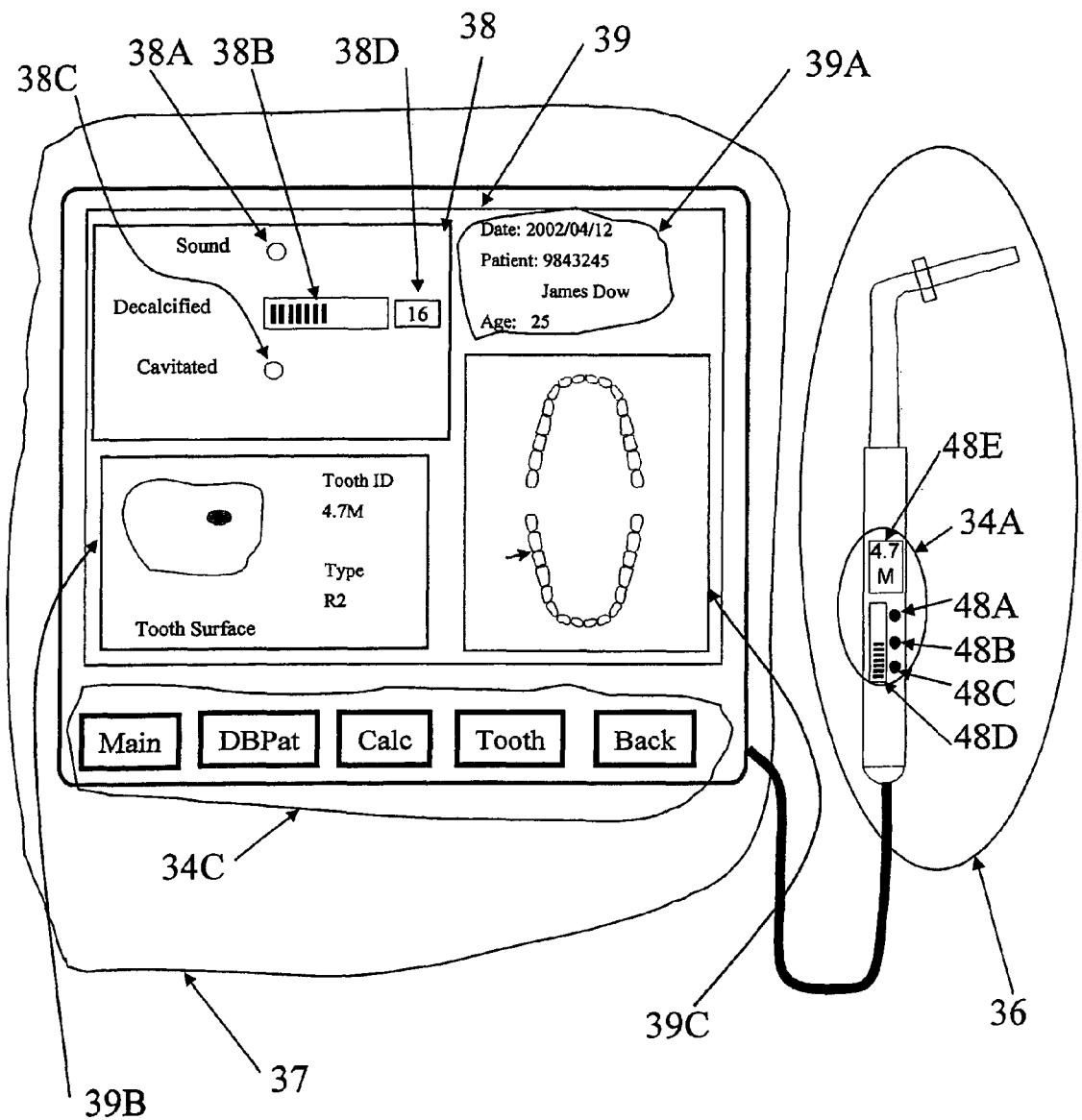
FIG. 17 is a schematic illustration of the apparatus for use in the methods of the present invention.
Figure 18:
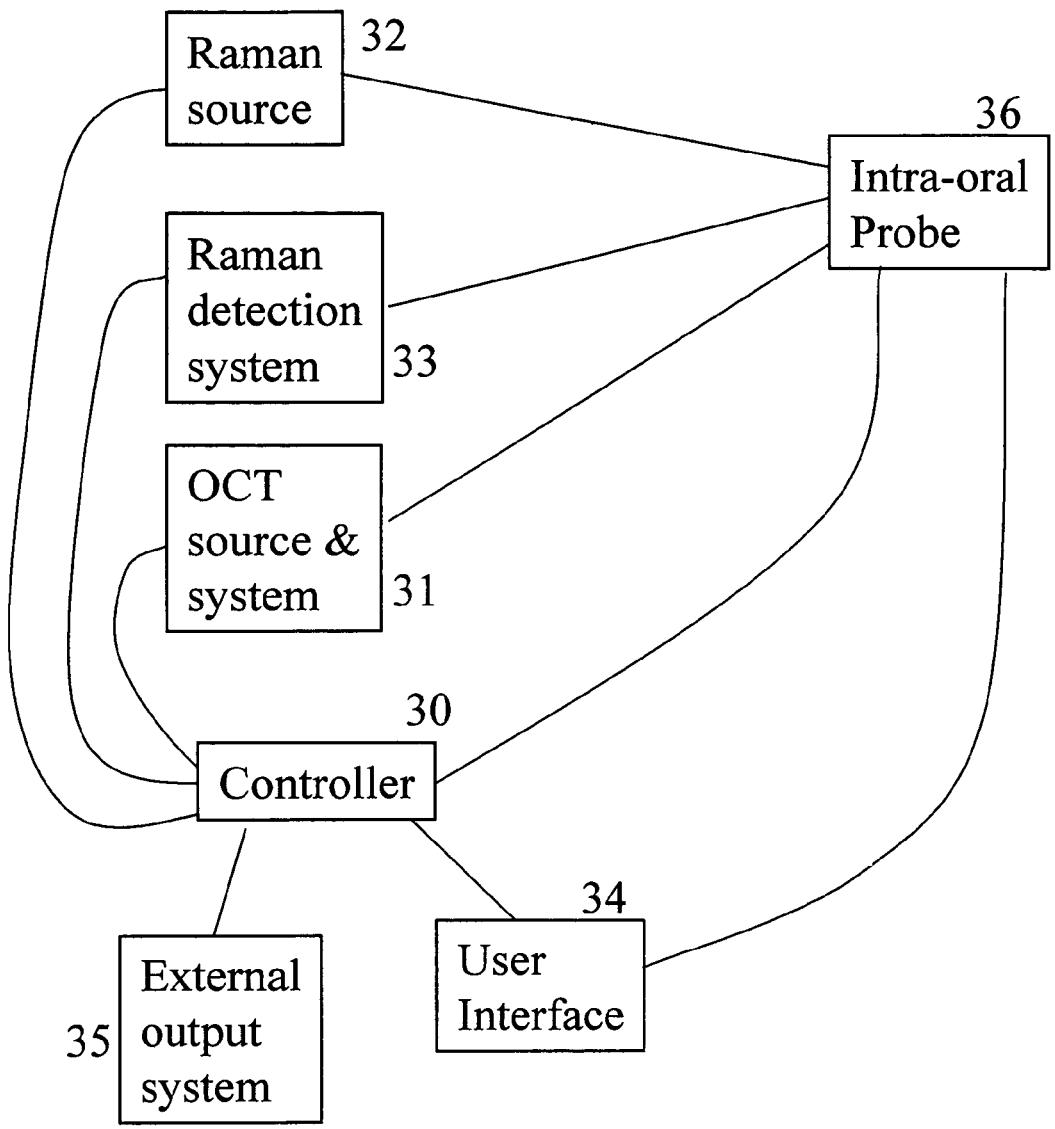
FIG. 18 is a block diagram of the apparatus of FIG. 17.

Turning now to the apparatus shown in FIGS. 17 to 25, the device for performing the measurements as shown in FIG. 18 includes a controller 30, OCT source and system 31, Raman source 32, Raman detection system 33, user interface 34, external output system 35 and an intra-oral probe 36. The controller unit 30 controls the device's operation and performs data manipulations. The controller interfaces with the OCT source and system 31, the Raman source 32, the Raman detection system 33 and the user interface 34. The intra-oral probe 36 is also interfaced to these components. The external output system may be a printer or communication interface to another device or other systems. FIG. 17 shows the main device 37 connected to the intra-oral probe 36. The user interface 34 includes display and user feedback controls 34A on the handle of the intra-oral probe 36 and display 39 and input controls 34C on the front of the main device 37. The user interface allows for the capture and linking of the patient information with the data from the intra-oral probe.

The user interface 34A on the intra-oral probe 36 consists of light indicators (green, yellow, red) 48A, 48B and 48C symmetrical to the indicators 38A, 38B and 38C on the main device 37 indicating action required and a bar indicator 48D of level of severity in the yellow region. This allows the operator to keep an eye on the handpiece and not on the LCD panel. The user interface 34A also includes a small display screen 48E which indicates the tooth surface currently under examination.

The user interface allows the user to select the tooth surface(s) of interest to scan and provides feedback on the results of the scan. The display and user feedback controls include an LCD 39 panel broken into several display regions and input via a touch screen menu 34C. The LCD 39 displays patient information 39A, the results of the tooth surface under examination 39B and the position for the tooth under examination 39C. The tooth surface's integrity is shown in the display region 38 which provides information on the soundness of the tooth's surface as either sound, decalcified or cavitated, as indicated by lights 38A, 38B and 38C. In addition to the surface integrity a measure of the degree of decalcification is indicated by a value and bar graph 38D. An image of the tooth surface is also displayed on the display region 39B indicating location(s) of the structural defect and a clinical measure of the defect. Both the main device and intra-oral probe have user interface buttons for input and displays for outputs.

The main device 37 connects to the intra-oral probe 36 via fiber optics and electrical signals. The intra-oral probe delivers light energy to the tooth surface for the techniques involved and provide a means of light energy reception to enable for the measurement required by the techniques. The techniques are OCT in either a traditional (polarized insensitive) mode or a polarized sensitive mode and Raman spectroscopy in either a traditional (polarized insensitive) mode or a polarized sensitive (PS) mode. Normally, the techniques are used in the visible and near infrared spectrum 400-2500 nm. Fiber optics are used to deliver light energy for both OCT and Raman spectroscopy to the sample and fiber optics to receive the returned light form the sample. OCT is capable using the same fiber optic for and delivery and reception of light to and from the sample through the use of fiber optic combiners and/or circulators. Raman spectroscopy normal makes use of separate delivery and reception fibers.

The OCT and Raman system normally operates at different wavelengths so as not to cause interference or crosstalk but a configuration in which the same source or wavelength is used for both could be possible. A possible common wavelength/source could make use of a high coherent source for Raman and wavelength swept the light energy for OCT. The sweeping of the source wavelength could also be used by the Raman system to collect spectra from multiple excitation wavelengths in order to mathematically remove the background fluorescence by generating a first derivative spectrum by subtracting two Raman spectra collected at two close wavelengths.

Figure 19:
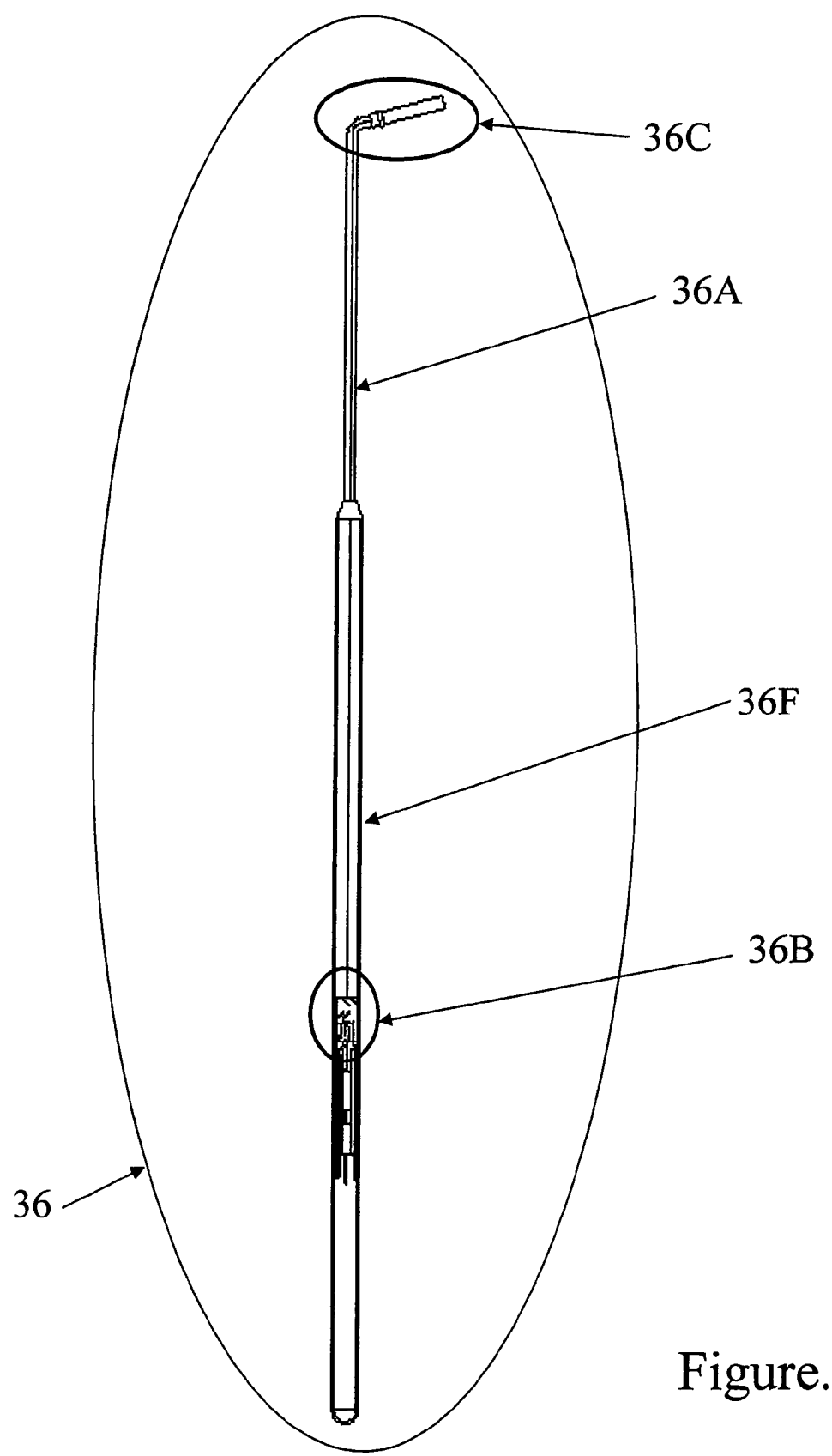
FIG. 19 is a side elevational view of a hand probe for use in the methods of the present invention.
Figure 20:
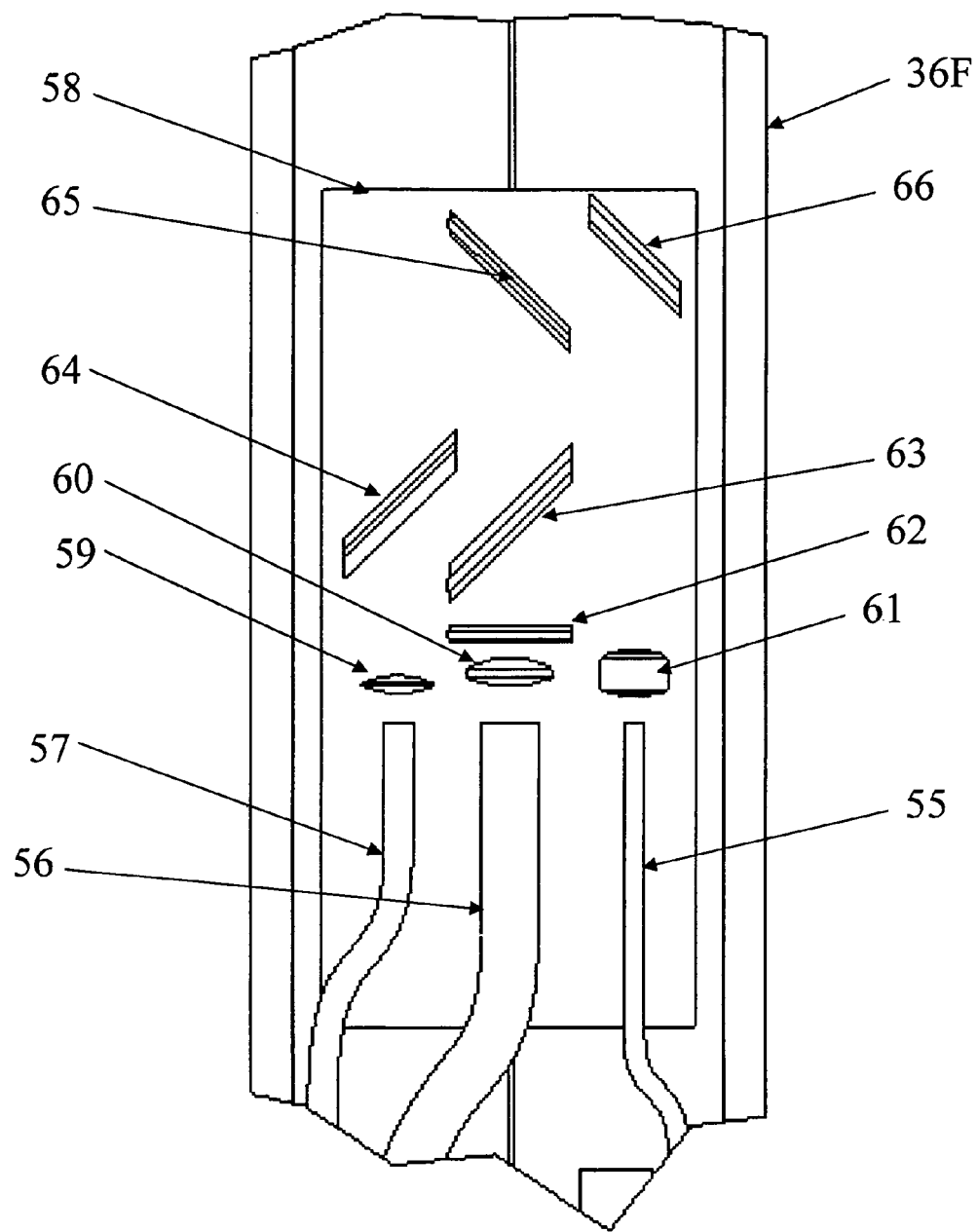
FIG. 20 is a side elevational view on an enlarged scale of a portion of the probe of FIG. 17 showing the operating internal components.

The device for performing the tooth measurements includes an intra-oral probe shown in FIG. 19. The intra-oral probe 36 consists of the main handpiece 36F and a hollow light tube 36A through which the light energy originating from the source/collector package 36B is launched down towards the probe scanning head 36C. The light tube 36A has an obtuse bend so that the handle section displaces the cheek from the user's line of site of the tooth they are inspecting with the device. The source/collector package is shown in detail in FIG. 20. The optical components of the source/collector package are mounted to the optics mounting platform 58. The fiber optics for the OCT delivery and reception 55, Raman delivery 57 and Raman reception 56. Each fiber bundle also has an associated optics package for collimation of the beam for launching down the light tube. The collimating optical packages are labeled 59 for Raman delivery, 60 for Raman reception and 61 for OCT delivery and reception. During OCT measurements, light is launched from the OCT fiber 55 and collimated by the optics package 61. The collimated beam then travels to the fixed mirror at 45 degrees 66 which steers the beam perpendicularly to the upright folding mirror at 45 degrees 65 causing the collimated beam to then proceed down the center of the handpiece 36F and into the light tube 36A. The returning OCT signal emanates as a collimated beam from the center of the light tube 36A. The returning beam follows the opposite optical path striking the upright folding mirror at 45 degrees 65 directing the beam onto the fixed mirror at 45 degrees 66. The collimated beam then passes though the optics package which focuses the beam onto the fiber optic.

During Raman configuration the folding mirror 65 is in a down position and removed from the optical path. The Raman delivery fiber 57 launches light into the collimating optics 59 which produces a collimated beam. The collimating optics 59 can also contain a sharp bandpass filter to remove unwanted wavelengths from source sidelobes or fiber fluorescence. The beam strikes the fixed mirror at 45 degrees 64 to the optical path causing the beam to proceed perpendicularly towards the dichroic beamsplitter 63 at 45 degrees to the optical path. The dichroic beamsplitter causes the collimated beam of Raman source light to travel down the center of the handpiece and into the center of the light tube 36A. The returning Raman light contains both elastically scattered Raman source light and inelastically scattered light which is red shifted to higher wavelengths. The returning Raman light emanates as a collimated beam from the center of the light tube 36A. The returning beam follows the opposite optical path striking the dichroic beamsplitter 63 at 45 degrees to the optical path. The dichroic beamsplitter 63 is tuned to a wavelength so that light below that wavelength, the returning elastically scattered Raman source light, is deflected as if the beamsplitter was a mirror at 45 degrees to the beam path. Light at wavelengths above the tuned wavelength, the inelastically scattered Raman light, is transmitted through the dichroic beamsplitter 63 towards the optical filter package 62. The optical filter package 62 contains a sharp cutoff filter to remove any remaining Raman source light. The collimated beam then passes through the optical package 60 which focuses the beam onto the fibers of the Raman reception fiber 56. The inside of the light tube 36A and main handpiece 36F are painted flat black to reduce stray light reflections.

Raman polarization measurements can be performed by adding a linear polarizer to the collimating optics 59 in the transmit path and polarization analyzing elements to the receive path in the optical filter package 62. The polarization analyzing elements can be fixed or manipulated to enable a variety of measurements types. Polarization measurements could be captured by the Raman detection system if polarization maintaining fiber optics are used. Polarization sensitive OCT measurements can be taken by using polarization maintaining fiber optics or through the use of polarization analyzing elements in the OCT collimation package 61. Polarization control methods can be accomplished by a number of methods including; inter-fiber filters, thin film filters on the fiber tips, bi-refringent optics (Wollaston prism), polarization maintaining fibers or wave plates as examples. Similarly, wavelength filtering can also be accomplished is a number of methods; Bragg fiber filters, thin film filters on the fiber ends, fiber profiles or geometries as examples.

Figure 21:
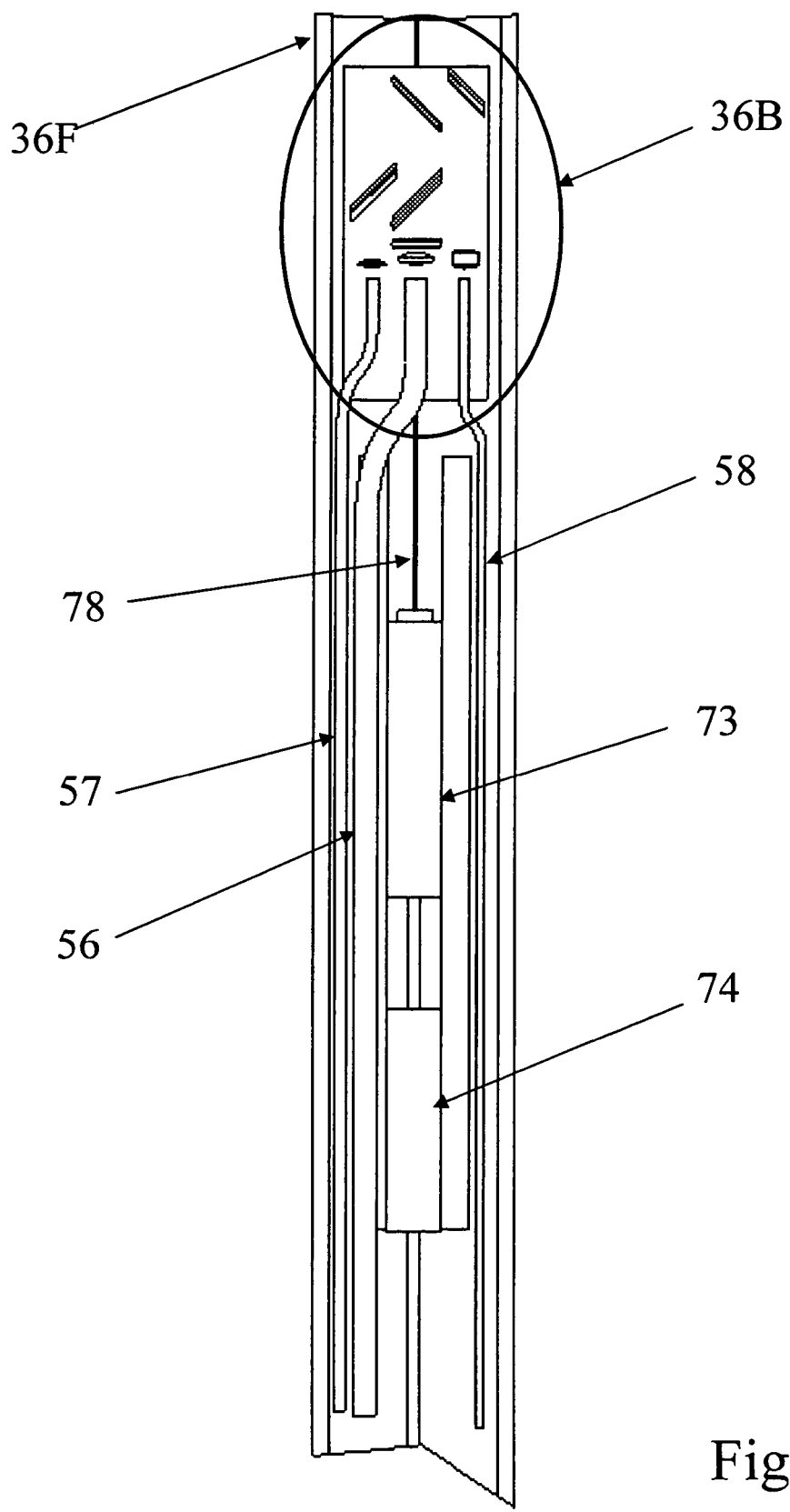
FIG. 21 is a side elevational view similar to FIG. 20 but showing additional parts.
Figure 22:
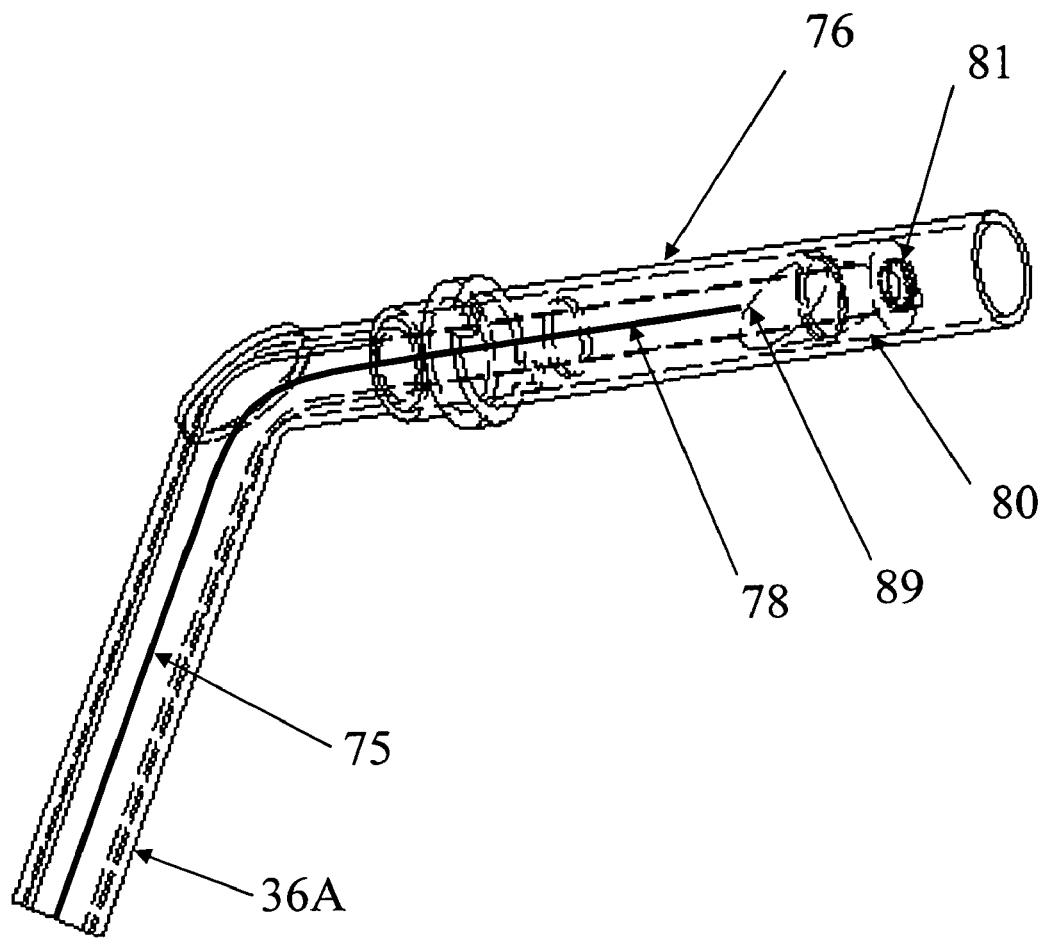
FIG. 22 is an isometric view of the tip of the probe of FIG. 21.

In FIG. 21, the mechanical drive components of the probe scanning head 36C are located behind the source/collector package 36B. A linear drive 74 and a rotational drive 73 are mechanically coupled to the probe scanning head 36C via an upper and lower control wires 78. The control wires travel along the inside of the top and bottom of the handpiece 36F and light tube 36A transferring mechanical motion to beam steering optics of the scanning head 36C. The probe scanning head is shown in FIG. 22. The control wires 78 pass along the top and bottom of the light tube 36A inside hollow wire guides 75 and then inside the probe guide 76. The upper control wire 78 connects to a linear slide 80 which carries a rotational ellipsoidal mirror 89 at 45 degrees to the incoming collimated optical beams. The upper control wire 78 transfers linear motion from the linear drive 74 to the ellipsoidal mirror 89 via the linear slide 80 which moves the beam along the length of the probe guide 76. The lower control wire 78 passes through the linear slide 80 to the rotational gearbox 81 which imparts rotation motion from the rotational drive 73 to the rotational ellipsoidal mirror 89 at 45 degrees. The rotation motion of the ellipsoidal mirror at 45 degrees 89 steers the beam in arcs, concentric about the probe guide 76.

Figure 23:
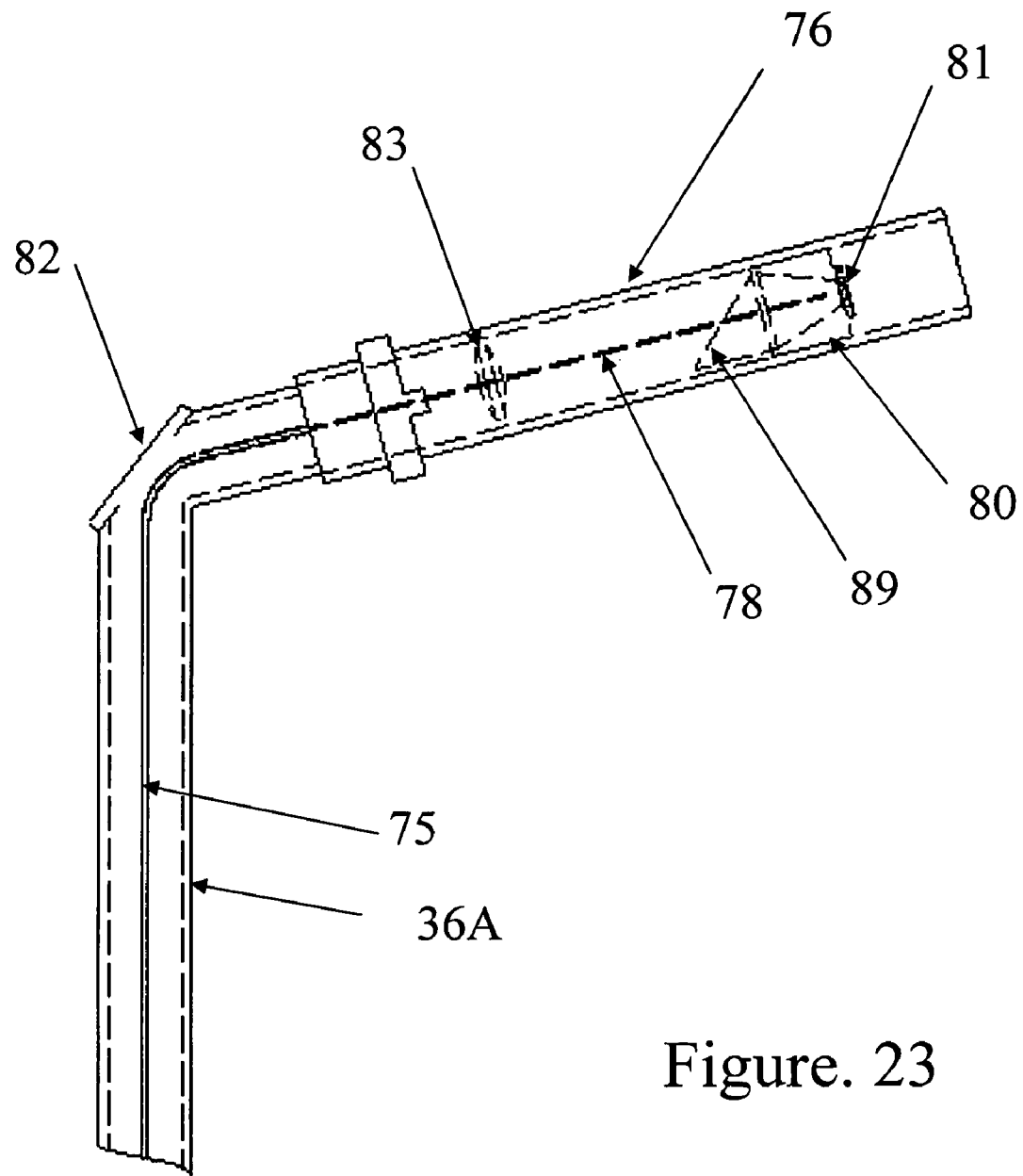
FIG. 23 is side elevational view of the probe of FIG. 22.
Figure 24:
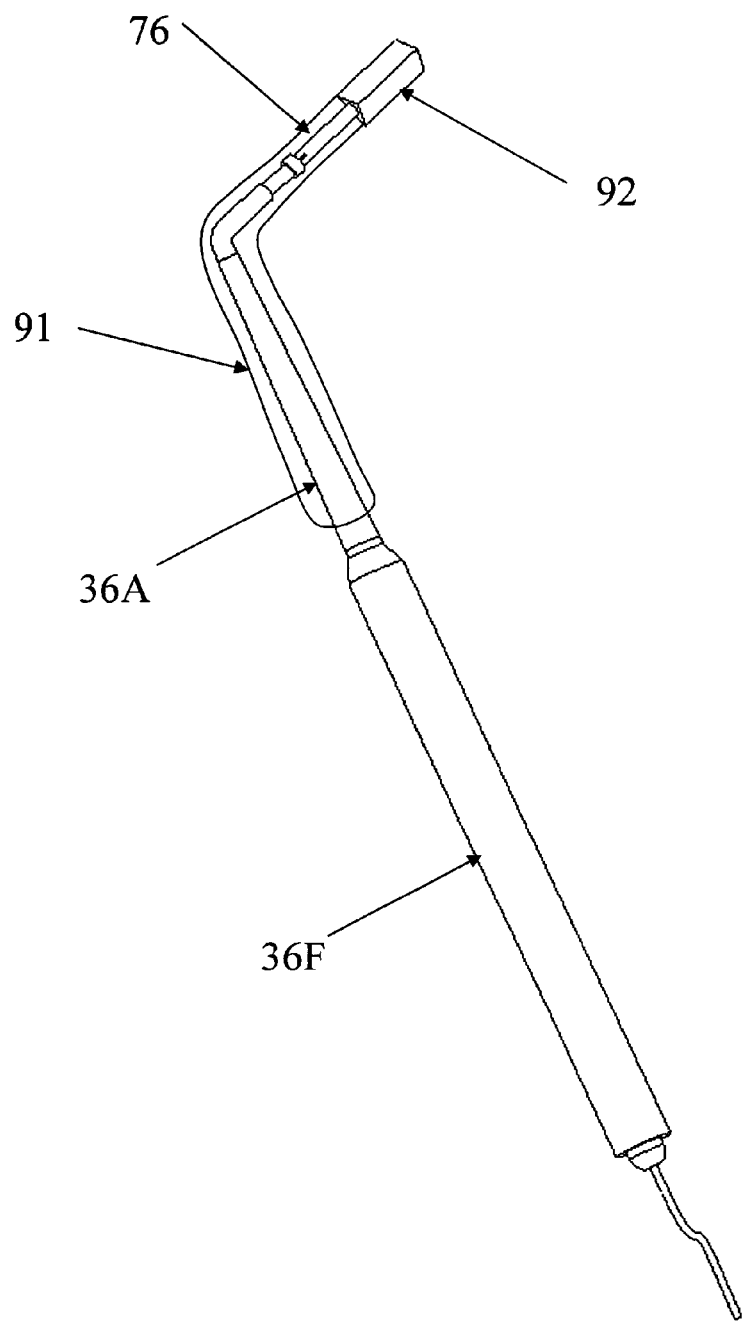
FIG. 24 is an isometric view of the handpiece showing an alternative shape of the tip of the probe.

In FIG. 23, the collimated light beams travel down the center of the light tube 36A from the handpiece 36F and strike the fixed ellipsoidal mirror 82 which turns the beam down the towards the center of the probe guide 76. The beam next passes through an optical package 83 which focuses the incoming collimated beam to a focal point. The optical package 83 is mounted relative to the ellipsoidal mirror 89 such that the focal plane of the light beams is at the tooth surface. The optical package can be move under control of the main device controller 30 with the addition of a second linear drive system. The movement of the optical package 83 can be used to adjust the focal plane relative to the tooth surface and for different wavelengths of the OCT and Raman systems. The optics contained in the optical package could have an adjustable numerical aperture through the use of deformable lens components which would enable different sample volumes by the depth of focus. The optical package 83 and ellipsoidal mirror 89 could be combined into a single concave mirror surface incorporating both reflective and focusing elements into a single component. The focusing beam then strikes the rotational ellipsoidal mirror 89 which turns the beam perpendicular to the transparent probe guide 76. The probe guide 76 is fitted with a transparent sterile probe tip sheath 92 which is shown in FIG. 24. The sterile probe tip sheath 92 butts against the flange on the probe guide 76 and locks into the keyways ensuring proper alignment with either the intra-oral probe seam in the top or down position relative to the intra-oral probe. The shape and two positions of the sterile probe tip sheath 92 allow for fitting the tip into the gingival embrasure space between two adjacent teeth and the gums of both the upper and lower jaw from the buccal or cheek side of the teeth. The probe tip sheath 92 also incorporates a flexible sheath 91 which covers the upper portion of the intra-oral probe for the prevention of contamination between patients. The probe tip sheath 92 can have a number of shape configurations as demonstrated in FIG. 25. The shape of the probe tip sheath 92 can be a fixed extruded shape as in the top of FIG. 25 or have a tapered shape as in the bottom of FIG. 25. The shape of probe tip sheath 92 allows the user to securely and repeatedly position probe in the gingival embrasure space. The intra-oral probe may incorporate a water flush line to irrigate the region around the probe tip sheath 92 to displace saliva and blood and act as an optical coupling fluid between the tooth surface and the probe tip sheath.

The ellipsoidal mirror 82 of the light tube 36A and the optical package 83 or ellipsoidal mirror 89 of the probe guide 76 can incorporate deformable optical elements to improve the optical efficiency of the imaging the tooth's surface. These optical elements can incorporate micro-electronic mirrors (MEMS), micro-optoelectrical mirrors (MOEMS) or galvanometer devices to allow steering of the light beam in a 2-dimensional (e.g. X-Y) pattern on the area of interest. These motions could also to be used for rapid stabilization for the light beam to ensure continuous measurement of the targeted sample area or volume by using feedback for acceleration sensors in the intra-oral probe 36.

For usage targeting the intra-proximal tooth surfaces, the probe tip of the intra-oral handpiece is placed in the gingival embrasure space. The shape of probe tip sheath 92 allows the user to securely position probe in the gingival embrasure space to minimize motion during the short scanning times. The base of the probe tip sheath not used for scanning purposes contains references markers which can be captured by the OCT and Raman systems to inform the system of the probe tip sheath's orientation. The probe guide 76 can also contain reference markers for system orientation confirmation and for validation of motion calibration. The controller configures the source/collector package 36B for OCT operation. The controller uses the linear and rotation drives in the probe to scan the mesial and/or distal surface of the tooth by controlling the motion of the ellipsoidal mirror in the probe scanning head 36C under control the linear and rotational drives. The result three dimensional morphological data is processed by the controller to identify suspect regions of structural defects. The controller then switches the optical platform to Raman configuration and positions the ellipsoidal mirror 89 in the probe guide 76 to sample the regions identified by OCT as suspect. Raman measurements are then taken of the suspect regions. The close coupling of the measurements of the two techniques allows the device to repeatedly measure the same tooth region matching the OCT and Raman diagnostics for confirmation of carious activity and tooth's current structural and biochemical status. These actions are repeated on all inspected tooth surfaces. Defects on a tooth surface are classified as sound, decalcified or cavitated. Unsound regions are further assigned a measure of the extent of decalcification. The OCT morphological information is used to classify carious regions based on their penetration depth relative to the anatomical dental and enamel junction (DEJ) using a scale of R0 to R3 where R0 is no enamel penetration, R1 is up to one half penetration, R2 is between one half and full penetration and R3 is dentin penetration. The device can store the acquired scans in a patient database. Using previous acquired OCT morphological scans and image registration techniques, data acquired at different time points of a tooth surface can be registered to each other for direct comparison of measurements. Such comparisons can be used to monitor tooth changes over time and for evaluation of treatment strategies. These comparisons are important since the demineralization and remineralization of mineralized tissues such as teeth are dynamic processes and knowledge of time series activity rate is important in forecasting the future risk of defect growth and reduction. The device also displays a pictogram of the patients mouth indicating which tooth is being probe or which results are being reviewed on screen by the user. The intra-oral handpiece also incorporates a small screen which can be rotated about the handpiece for easy of viewing during contralateral handpiece usage. The handpiece has trigger buttons for the user to trigger data collection or switching between mesial and distal scanning modes. The device can be used with a multitude of handpiece configurations for targeting other tooth surfaces or for endoscopic probes for targeting bones or other internal mineralized tissue deposits or structures.

Since various modifications can be made in our invention as herein above described, and many apparently widely different embodiments of same made within the spirit and scope of the claims without department from such spirit and scope, it is intended that all matter contained in the accompanying specification shall be interpreted as illustrative only and not in a limiting sense.

REFERENCES

1. Anonymous, "Diagnosis and management of dental caries throughout life. National Institutes of Health Consensus Development Conference statement, Mar. 26-28, 2001", *J. Dent. Educ.* 65, 1162-8 (2001).
2. US Department of Health and Human Services, "Oral Health in America: A Report of the Surgeon General—Executive Summary." Rockville, Md.: US Department of Health and Human Services, National Institute of Dental and Craniofacial Research, National Institutes of Health (2000).
3. G. K. Stookey, R. D. Jackson, A. G. Zandona, and M. Analoui, "Dental caries diagnosis", *Dent Clin. North Am.* 43, 665-77 (1999).
4. G. K. Stookey and C. Conzalez-Cabezas, "Emerging methods of caries diagnosis", *J. Dent. Educ.* 65, 1001-1006 (2001).
5. C. A. Murdoch-Kinch, "Oral medicine: advances in diagnostic procedures.", *J. Calif. Dent. Assoc.* 27, 773-80 (1999).
6. A. Hall and J. M. Girkin, "A review of potential new diagnostic modalities for caries lesions", *J. Dent. Res.* 83, C89-C94 (2004).
7. A. Schneiderman, M. Elbaum, T. Shultz, S. Keem, M. Greenebaum and J. Driller, "Assessment of dental caries with digital imaging fibre-optic transillumination (DI-FOTI): in vitro study", *Caries Res.* 31, 103-10 (1997).
8. B. T. Amaechi and S. M. Higham, "Quantitative light-induced fluorescence: A potential tool for general dental assessment", *J. Biomed. Opt.* 7, 7-13 (2002).
9. X. Q. Shi, U. Welander, U. and B. Angmar-Mansson, "Occlusal caries detection with KaVo DIAGNOdent and radiography: an in vitro comparison", *Caries Res.* 34, 151-8 (2000).
10. A. Lussi, B. Megert, C. Longbottom, E. Reich and P. Francescut, "Clinical performance of a laser fluorescence device for detection of occlusal caries lesions", *Eur. J. Oral Sci.* 109, 14-9 (2001).
11. C. Robinson, R. C. Shore, S. J. Brookes, S. Strafford, S. R. Wood and J. Kirkham, "The chemistry of enamel caries", *Crit. Rev. Oral. Biol. Med.*, 11, 481-495 (2000).
12. L. M. Silverstone, "Structure of carious enamel, including the early lesion", *Oral. Sci. Rev.* 3, 100-160 (1973).
13. D. J. White, "The application of in vitro models to research on demineralizaton and remineralizatoin of the teeth", *Adv. Dent. Res.* 9, 175-193 (1995).
14. F. I. Feldchtein, G. V. Gelikonov, V. M. Gelikonov, R. R. Iksanov, R. V. Kuranov, A. M. Sergeev, N. D. Gladkova, M. N. Ourutina, J. A. Warren Jr. and D. H. Reitze, "In vivo OCT imaging of hard and soft tissue of the oral cavity.", *Opt. Express* 3, 239-250 (1998).
15. A. Baumgartner, S. Dichtl, C. K. Hitzenberger, H. Sattmann, B. Robl, A. Moritz, A. F. Fercher and W. Sperr, W. "Polarization-sensitive optical coherence tomography of dental structures", *Caries Res.* 34, 59-69 (2000).
16. B. W. Colston Jr., M. J. Everett, U. S. Sathyam, L. B. DaSilva, and L. L. Otis, "Imaging of the oral cavity using optical coherence tomography", *Monogr. Oral Sci.* 17, 32-55 (2000).
17. B. T. Amaechi, S. M. Higham, A. G. Podoleanu, J. A. Rogers, and D. A. Jackson, "Use of optical coherence tomography for assessment of dental caries: quantitative procedure", *J. Oral Rehabil.* 28, 1092-3 (2001).
18. C. K. Hitzenberger, E. Gotzinger, M. Sticker, M. Pircher and A. F. Fercher, "Measurement and imaging of birefringence and optic axis orientation by phase resolved polarization sensitive optical coherence tomography", *Opt. Express* 9, 780-790 (2001).
19. D. Fried, J. Xie, S. Shafi, J. D. B. Featherstone, T. M. Breunig and C. Le, "Imaging carious lesions and lesion progression with polarization sensitive optical coherence tomography", *J. Biomedical Opt.* 7, 618-627 (2002).
20. E. B. Hanlon, R., Manoharan, T. W. Koo, K. E. Shafer, J. T. Motz, M. Fitzmaurice, J. R. Kramer, I. Itzkan, R. Dasari, and M. Feld, "Prospects for in vivo Raman spectroscopy", *Phys. Med. Biol.* 45, R1-R59 (2000).
21. H. Tsuda and J. Arends, "Raman spectroscopy in dental research: a short review of recent studies", *Adv. Dent Res.* 11, 539-47 (1997).
22. M. T. Kirchner, H. G. M. Edwards, D. Lucy and A. M. Pollard, "Ancient and modern specimens of human teeth: a Fourier transform Raman spectroscopic study", *J. Raman Spectrosc.* 28, 171-178 (1997).
23. S. Stewart, D. A. Shea, C. P. Tarnowski, M. D. Morris, D. Wang, R. Franceschi, D.-L. Lin and E. Keller, "Trends in early mineralization of murine calvarial osteoblastic cultures: a Raman microscopic study", *J. Raman Spectrosc.* 33, 536-543 (2002).
24. A. Carden and M. D. Morris, "Application of vibrational spectroscopy to the study of mineralized tissues (review)", *J. Biomed. Opt* 5, 259-268 (2000).
25. A. Carden, R. M. Rajachar, M. D. Morris and D. H. Kohn, "Ultrastructural changes accompanying the mechanical deformation of bone tissue: A Raman imaging study", *Calcif. Tissue Int.* 72, 166-175 (2003).
26. J. A. Timlin, A. Carden and M. D. Morris, "Raman spectroscopic imaging markers for fatigue-related microdamage in bovine bone", *Anal. Chem.* 72, 2229-2236 (2000).
27. H. Ou-Yang, E. P. Paschalis, A. L. Boskey, R. Mendelsohn, "Two-dimensional vibrational correlation spectroscopy of in vitro hydroxyapatite maturation", *Biopolymers* 57, 129-139 (2000).
28. Y. Leung and M. D. Morris, "Characterization of the effects of postextraction treatments on human dentin-resin interface by micro-Raman spectroscopy", *J. Biomed. Opt.* 2, 120-124 (1997).
29. E. Wentrup-Byrne, C. A. Armstrong, R. S. Armstrong and B. M. Collins, "Fourier transform Raman microscopic 29. mapping of molecular components in a human tooth," *J. Raman Spectrosc.* 28, 151-158 (1997).
30. P. Tramini, B. Pelissier, J. Valcarcel, B. Bonnet and L. Maury, "A Raman spectroscopic investigation of dentin and enamel structures modified by lactic acid", *Caries Res.* 34, 233-240 (2000).
31. J. Xu, I. Stangel, I. S. Butler and D. F. R. Gilson, "An FT-Raman spectroscopic investigation of dentin and collagen surfaces modified by 2-hydroxyethylmethacrylate", *J. Dent. Res.* 76, 596-601 (1997).
32. R. M. Lemor, M. B. Kruger, D. M. Wieliezka, J. R. Swafford and P. Spencer, "Spectroscopic and morphologic characterization of the dentin/adhesive interface", *J. Biomed. Opt.* 4, 22-7 (1999).
33. R. Lemoi. M. B. Kruger, D. M. Wieliczka, P. Spencer and T. May, "Dentin etch chemistry investigated by Raman and infrared spectroscopy", *J. Raman Spectrosc.* 31, 171-176 (2000).
34. P. Spencer, Y. Wang, M. P. Walker, D. M. Wieliczka and J. R. Swafford, "Interfacial chemistry of the dentin/adhesive bond", *J. Dent. Res.* 79, 1458-1463 (2000).
35. B. van Meerbeek, H. Mohrbacker, J. P. Celis, J. R. Roos, M. Braem, P. Lambrechts and G. Vanherle, "Chemical characatization of the resin-dentin interface by micro-Raman spectroscopy", *J. Dent. Res.* 72, 1423-1428 (1993).
36. H. Tsuda and J. Arends, "Orientational micro-Raman spectroscopy on hydroxyapatite single crystals and human enamel crystallites", *J. Dent. Res.* 73, 1703-1710 (1994).
37. G. Leroy, G. Penel, N. Leroy and E. Bres, "Human tooth enamel: a Raman polarized approach", *Appl. Spectrosc.* 56, 1030-1034 (2002).
38. W. Hill and V. Petrou, "Detection of caries and composite resin restorations by near-infrared Raman spectroscopy", *Appl. Spectrosc.* 51, 1265-1268 (1997).
39. W. Hill and V. Petrou, "Caries detection by diode laser Raman spectroscopy", *Appl. Spectrosc.* 54, 795-799 (2000).
40. D. Fried, R. E. Glena, J. D. B. Featherstone and W. Seka, "Nature of light scattering in dental enamel and dentin at visible and near-infrared wavelengths", *Appl. Opt* 34,1278-1285 (1995).
41. E. S. Etz, W. S. Hurst and S. J. Choquette, "Raman intensity calibration with glass luminescence standards", *Inst Phys. Conf Ser.* 165, 121-122 (2000).
42. K. G. Ray and R. L. McCreery, "Simplified calibration of instrument response function for Raman spectrometers based on luminescent intensity standards", *Appl. Spectrosc.* 51, 108-116 (1997).
43. K. J. Frost and R. L. McCreery, "Calibration of Raman spectrometer instrument response function with luminescence standards: An update", *Appl. Spectrosc.* 52, 1614-1618 (1998).
44. G. Penel, G. Leroy, C. Rey and E. Bres, "MicroRaman spectral study of the $PO_4$ and $CO_3$ vibrational modes in synthetic and biological apatites", *Calcif. Tissue Int.* 63, 475-481 (1998).
45. J. J. Freeman, B. Wopenka, M. J. Silva and J. D. Pasteris, "Raman spectroscopic detection of changes in bioapatite in mouse femora as a function of age and in vitro fluoride treatment", *Calcif. Tissue Int.* 68, 156-162 (2001).
46. J. D. Pasteris, B. Wopenka, J. J. Freeman, K. Rogers, E. Valsami-Jones, J. A. M. van der Houwen and M. J. Silva, "Lack of OH in nanocrystalline apatite as a function of degree of atomic order: implications for bone and biomaterials", *Biomaterials* 25, 229-238 (2004).
47. R. Z. LeGeros, "Chemical and cystallographical events in the caries process", *J. Dent. Res.* 69, 567-574 (1990).
48. F. F. M. de Mul, M. H. J. Hottenhuis, P. Bouter, J. Greve, J. Arends and J. J. ten Bosch, "Micro-Raman line broadening in synthetic carbonated hydroxyapatite", *J. Dent. Res.* 65, 437-440 (1986).
49. C. Robinson, J. A. Weatherell and J. Kirkham, "The Chemistry of Dental Caries," in *Dental Enamel: Formation to Destruction*, C. Robinson, J. Kirkham and R. Shore, Eds., pp. 223-243, CRC Press Inc. Boca Raton (1995).
50. A. S. Hallsworth and C. Robinson, "Loss of carbonate during the first stages of enamel caries", *Caries Res.* 7, 345-348 (1973).
51. C. Robinson, J. A. Weatherell and A. S. Hallsworth, "Alterations in the composition of permanent human enamel during caries attack" in *Demineralisation and Remineralisation of the Teeth*, S. A. Leach and W. M. Edgar, Eds., IRL Press, Oxford, p. 209, 1983.
52. J. C. Elliot, "Mineral, synthetic and biological carbonate apatites" in *Structure and Chemistry of the Apatites and Other Calcium Orthophosphates*, Elsevier, New York, pp. 191-304 (1994).
53. J. A. Weatherell, C. Robinson and C. R. Hiller, "Distribution of carbonate in thin sections of dental enamel" *Caries Res.* 2, 1-9 (1968).

The invention claimed is:

1. A method for detecting and/or monitoring changes in mineralized tissues or calcified deposits comprising:
    scanning an area of mineralized tissues or calcified deposits using optical coherence tomography (OCT) to generate OCT data which is used for detection and assessment of any location containing a change therein;
    and, on detection from the OCT data of a change at a location, using Raman spectroscopy over a part of the area including the location containing the change and excluding some of the area remote from the location to generate Raman data which is used to detect, confirm or monitor the change therein.

2. The method according to claim 1 wherein the OCT is used to scan a whole area for areas of interest and the Raman spectroscopy is used only in the locations containing the changes identified by the OCT data.

3. The method according to claim 1 wherein the OCT and the Raman spectroscopy are carried out using a common probe.

4. The method according to claim 3 wherein the OCT and the Raman spectroscopy are carried out without moving the probe between measurements.

5. The method according to claim 1 wherein the OCT and the Raman spectroscopy are carried out sequentially.

6. The method according to claim 1 wherein the OCT uses polarized light.

7. The method according to claim 1 wherein the OCT data is used to provide morphological details comprising:
    Size;
    Depth within tissue;
    Shape;
    Border delineating area of interest from surrounding material;
    Indication of heterogeneity of sample;
    Presence of cracks or defects;
    Boundary between different tissue layers or tissue types.

8. The method according to claim 1 wherein Raman spectroscopy data is used to provide biochemical information for confirming that regions arising from genetic or developmental malformations detected by the optical coherence tomography as areas of interest are false-positive results of early diseased states.

9. The method according to claim 1 wherein the Raman spectroscopy is carried out at a wavelength in the near-infrared range (e.g. 830 nm within 750 nm-2500 nm range) as the background biological fluorescence is lower in this range.

10. The method according to claim 1 wherein the Raman spectroscopy is carried out at a wavelength of 750 nm-1000 nm which allows for Raman signal detection by silicon-based detectors (CCD).

11. The method according to claim 1 wherein the detection and monitoring in the Raman spectroscopy is carried out using biochemical information derived from the ratio of various selected Raman peaks to the P-O symmetric stretching vibration (nu1 peak) of hydroxyapatite (e.g. ~930 cm$^{-1}$-1000 cm$^{-1}$) peak.

12. The method according to claim 1 wherein the Raman spectroscopy uses selected peaks specific to Raman bands arising from hydroxyapatite and related calcium phosphates found within mineralized tissues and calcified deposits, comprising Raman shift in the spectral regions between 200-1200 cm$^{-1}$.

13. The method according to claim 1 wherein the Raman spectroscopy uses polarized light.

14. The method according to claim 13 wherein polarization-coupled techniques are used to quantitate the change in demineralization and remineralization which alter the birefringent properties of the sample.

15. The method according to claim 1 wherein the Raman spectroscopy uses polarized light and compares signals with parallel polarized and perpendicular polarized light comprising:
determining the depolarization ratio, $\rho$ $\rho = I_{(\perp)}/I_{(\parallel)}$ where $I_{(\perp)}$ and $I_{(\parallel)}$ are the integrated peak intensities of the P-O symmetric stretching vibration (nu1 peak) of hydroxyapatite (e.g. ~930 cm$^{-1}$-1000 cm$^{-1}$) in orthogonally polarized Raman spectra.

16. The method according to claim 1 wherein the Raman spectroscopy uses polarized light and compares signals with parallel polarized and perpendicular polarized light and quantification of the anisotropic difference is achieved by using the following equation:

$A = (1-\rho)/(1+2\rho)$ with $\rho = I_{(\perp)}/I_{(\parallel)}$ or $A = (I_{(\parallel)} - I_{(\perp)})/(I_{(\parallel)} + 2I_{(\perp)})$ Where A is anisotropy or sometimes called the conventional index of orientation.

17. The method according to claim 1 wherein the Raman spectroscopy is used to detect changes in structure, orientation, crystallinity and/or chemistry of hydroxyapatite and/or calcium phosphate crystals and/or rods in the sample.

18. The method according to claim 17 wherein the Raman spectroscopy data is used to provide information of the mineralization state:
Active or arrested dental caries;
Degree of demineralization;
Degree of remineralization;
Degree of hypermineralization.

19. The method according to claim 1 wherein there is provided a high coherent light source for the Raman spectroscopy which is also capable of wavelength sweeping to provide broadband light energy for the OCT.

20. The method according to claim 1 wherein light energy for the OCT and the Raman spectroscopy is delivered to the sample and signal collected from the sample via at least one fibre optic cable and wherein the same fibre optic is used for delivery and collecting the light to and from the sample through the use of fibre optic combiners and/or circulators.

21. The method according to claim 1 wherein light energy for the OCT and the Raman spectroscopy is delivered to the sample and signal collected from the sample via at least one fibre optic cable and wherein the probe contains optical components enabling controlling the transmission and reception of the light energy so that the area of interest is scanned.

22. The method according to claim 21 wherein the optical components comprise steerable mirrors such as micro-electronic mirrors (MEMS) or micro-optoelectrical mirrors (MOEMS) or galvanometer devices or rotation motors or translational motors to allow steering of the light beam in a 2-dimensional (e.g. X-Y) pattern on the area of interest and an optical path switcher to toggle between OCT and Raman spectroscopy and wherein the probe has internal reference markers to enable validation of the 2-dimensional pattern.

23. The method according to claim 1 wherein light energy for the OCT and the Raman spectroscopy is delivered to the sample and signal collected from the sample via at least one fibre optic cable and wherein the probe contains optical filters such as bandpass filters for selecting the wavelengths of interest for Raman measurements or optical filters such as longpass filter, edge filter or notch filters or fibre Bragg gratings for blocking/suppressing the Rayleigh scatter and transmitting the Raman scattered signal.

24. The method according to claim 1 wherein light energy for the OCT and the Raman spectroscopy is delivered to the sample and signal collected from the sample via at least one fibre optic cable and wherein the probe contains optical components to allow optional polarization studies such as linear polarizers, analyzers, waveplates, beam splitter and birefringent optics.

25. The method according to claim 1 wherein there is provided a portable LCD control box which can provide data analysis to overlay data and produce user-friendly data for clinicians/operators.

26. The method according to claim 1 wherein the OCT data is used to generate images which are processed allowing automatic determination of the sample surface, determination of the DEJ, determination of the scattering intensity in order to arrive at a quantitative value regarding:
presence of an intact surface;
lesion depth;
thickness of the surface layer.

27. The method according to claim 1 wherein the OCT data is arranged such that there are image registration markers enabling the use of time series of OCT images to allow spatial registration of data collected for monitoring and comparison purposes where such information relays information of lesion progression, activity, arrest, reduction, demineralization and remineralization.

28. The method according to claim 1 wherein the Raman data is processed to obtain the level of remineralization from the intensity of the $CaF_2$ and/or fluoroapatite peak at 300-350 cm$^{-1}$ and/or between the spectral range of 200-1200 cm$^{-1}$.

29. The method according to claim 1 wherein the Raman spectroscopy is carried out using a sweeping of the source wavelength which is used by the Raman spectroscopy to collect data from multiple excitation wavelengths (e.g. differing by 1 nm) in order to mathematically remove the background fluorescence signals by taking a difference of the data acquired at each wavelength and integrating the resulting difference to produce Raman data free of the background fluorescence.

30. A method for detecting and/or monitoring changes in tooth enamel or dentin for the detection of dental caries comprising:

scanning an area of tooth enamel or dentin using optical coherence tomography (OCT) to generate OCT data which is used for and assessment of any location containing a change therein;

and, on detection from the OCT data of a change at a location, using Raman spectroscopy over a part of the area including the location containing the change and excluding some of the area remote from the location to generate Raman data which is used to detect, confirm or monitor the change therein.

31. The method according to claim 30 wherein the OCT and Raman spectroscopy data are used in analysis of dental caries to provide quantitative information about the dental caries comprising:

Estimate of the lesion depth;

degree of demineralization based on the depolarization ratio or anisotropy or conventional index of orientation;

degree of remineralization and hypermineralization based upon the depolarization ratio or anisotropy or conventional index of orientation and/or the peak positions/widths (e.g. full-width half maximum) of the spectra between 200-1200 $cm^-$ and/or the intensity of the $CaF_2$ peak around 300-350 $cm^-$ in the Raman spectrum arising from calcium fluoride or fluoroapatite upon remineralization.

32. The method according to claim 30 wherein light energy for the OCT and the Raman spectroscopy is delivered to the sample and signal collected from the sample via at least one fibre optic cable interfaced with an ergonomically-shaped dental handpiece probe with an intra-oral portion and a probe shaft and wherein the probe shaft is wrapped in disposable sterile sheath.

33. The method according to claim 30 wherein light energy for the OCT and the Raman spectroscopy is delivered to the sample and signal collected from the sample via at least one fibre optic cable interfaced with an ergonomically-shaped dental handpiece probe with an intra-oral portion and the probe contains a linear and rotation motors and mechanics allowing for full rotation to enable sequential measurements from two adjacent surfaces of the distal and mesial surfaces of a tooth.

34. The method according to claim 33 wherein the probe contains an indicator of which surface of the tooth is currently under investigation.

35. The method according to claim 30 wherein light energy for the OCT and the Raman spectroscopy is delivered to the sample and signal collected from the sample via at least one fibre optic cable interfaced with an ergonomically-shaped dental handpiece probe with an intra-oral portion and wherein the probe contains a probe head and tip arranged to enable imaging/measurements in the gingival embrasure of the interproximal spaces between adjacent teeth, the tip having a triangular cross-section to allow the tip to be wedged into tight spaces such as the gingival embrasures between teeth, the tip being formed of a material that allows transmission and collection of light energy with minimal disruption.

36. The method according to claim 35 wherein the probe tip is capable of rotating 180 degrees for functioning such as in all four quadrants of a mouth.

37. The method according to claim 30 wherein Raman data is processed to obtain depolarization ratio values and/or anisotropy index of orientation values useful for Indicating the presence of sound enamel;
Indicating the presence of early dental caries;
Indicating the activity and severity of the dental caries.

38. The method according to claim 30 wherein there is provided a user interface in the form of an LDC control box for data acquisition which includes an LCD screen display for displaying which surface of a tooth is under test and which quadrant/tooth number.

39. The method according to claim 30 wherein there is provided a user interface in the form of an LDC control box for data acquisition which includes separate indicators indicative of no decalcification, decalcification and intact surface and cavitation together with a numerical scale to indicate depth, activity or severity of demineralization.

40. The method according to claim 30 wherein there is provided a handpiece which contains separate indicators indicative of no decalcification, decalcification and intact surface and cavitation.

* * * * *